| United States Patent [19] | [11] Patent Number: 4,977,137 |
| Nichols et al. | [45] Date of Patent: Dec. 11, 1990 |

[54] LACTOFERRIN AS A DIETARY INGREDIENT PROMOTING THE GROWTH OF THE GASTROINTESTINAL TRACT

[75] Inventors: Buford L. Nichols; Kathryn S. McKee, both of Houston, Tex.

[73] Assignee: Baylor College of Medicine, Houston, Tex.

[21] Appl. No.: 57,562

[22] Filed: Jun. 3, 1987

[51] Int. Cl.$^5$ ............... A61K 37/14; A61K 37/02; A23L 1/305
[52] U.S. Cl. .................. 514/6; 514/21; 514/867; 426/74; 426/801
[58] Field of Search ........... 514/21, 6, 867; 426/74, 426/801

[56] References Cited

U.S. PATENT DOCUMENTS 4,668,771  5/1987  Kawakami et al. .................. 530/366
4,726,948  2/1988  Prieels et al. ...................... 424/94.4

*Primary Examiner*—Jacqueline Stone
*Attorney, Agent, or Firm*—Fulbright & Jaworski

[57] ABSTRACT

Disclosed is milk lactoferrin as a dietary ingredient which promotes growth of the gastrointestinal tract of human infants and newborn nonhuman animals immediately on birth when added to an infant formula or given separately as a dietary supplement thus reducing chronic diarrhea, assisting in the management of short gut syndrome, and avoiding, at least to some extent, chronic intractable diarrhea of the infant.

27 Claims, 16 Drawing Sheets

LACTOFERRIN AS A DIETARY INGREDIENT PROMOTING THE GROWTH OF THE GASTROINTESTINAL TRACT

FIELD OF THE INVENTION

The present invention is in the field of dietary supplementation of newborn human infants and newborn animals.

BACKGROUND OF THE INVENTION

A substantial growth of the intestines of newborn animals takes place in the first one to three days after birth. For example, in newborn pigs who are nursed by the mother, there is a substantial growth, approximately eight to ten inches, of the intestines of the infant within the first few days after birth. In a large number of human newborns, who are not nursed by the mother but are placed on an infant's formula, this growth of the gastrointestinal tract during the first few days may not occur, and, as a result, the infant is predisposed to chronic intractable diarrhea which must be managed for a period of three or more months at considerable expense and discomfort to the infant.

The present invention is based upon the discovery that milk lactoferrin as a dietary ingredient promotes the growth of the gastrointestinal tract when added to infant formula or given separately from the formula and thus reduces the occurrence of chronic diarrhea and may assist in the management of short-gut syndrome and avoids, at least to some extent, chronic intractable diarrhea of the infant. The lactoferrin may be from a nonhuman animal or human source. The milk containing the lactoferrin should not be processed, such as by pasturization or the lactoferrin processed, extracted, or purified by a process which destroys the effectiveness of the lactoferrin.

Mammary secretions from goats, sheep, cows, and humans have been found to stimulate the proliferation of various cell lines growing in culture (1-3). When purified, the active factor was found to be Epidermal Growth Factor (EGF). None of the cell lines used for the bioassay of previous mitogenic factors exhibit polarity and none have brush border membranes.

In a search for factors in human colostrum which might stimulate enterocyte proliferation, we developed an assay for thymidine incorporation into DNA using harvested crypt cells from mature rat small intestine. Whole skimmed human colostrum stimulated a significant increase in thymidine incorporation into crypt cell DNA during a 60 minute period of incubation. When the protein with biological activity was purified to a single peak by sequential ion and gel chromatography, it was found to have the characteristics of lactoferrin. The mobility of SDS electrophoresis and electrofocusing was identical to that of standard lactoferrin. The protein was identical to these standards on double-diffusion immunologic testing. All available human lactoferrins stimulated thymidine uptake and all reacted with a lactoferrin polyclonal antibody. Human lactoferrin appears to be a potent activator of thymidine incorporation into DNA in incubated rat crypt cells, a biological activity not previously reported.

In addition, we found that EGF does not stimulate crypt cells. This finding supports our hypothesis that the response of 3T3 fibroblasts to EGF is not synonymous with a trophic effect on polarized intestinal epithelial cells.

Studies in the pig, dog, and rat indicate that the gastrointestinal tract matures more rapidly if the newborn animal is suckled (1-3). The nutritional significance of these observations lies in the principle that the structure of ingested protein may have biological significance beyond the dietary requirement for amino acids. Based on these observations, in vitro fibroblasts and other cell lines have been used to test for the presence of growth-promoting factors in milk. Mammary secretions from goats, sheep, cows, and humans have been found to stimulate the proliferation of various cell lines growing in culture (4-6). A portion of the activity in fibroblast culture can be attributed to EGF, a 6000-$M_r$ mitogen present in many mammalian secretions (7). Other factors with mitogenic activity, however, have been identified, e.g. polypeptides with $M_r$ of approximately 140,000 and 36,000(5).

None of the cell lines used for the bioassay of mitogenic factors exhibit polarity and none have brush-border membranes. Assuming that specificity may exist in intestinal cells, we developed a bioassay based on harvested rat crypt enterocytes. The bioassay works equally well with harvested pig crypt enterocytes. With this assay, we have confirmed the presence of mitogenic activity in human colostrum. Subsequently set forth herein are the details of the bioassay, the isolation of lactoferrin as a mitogenic dietary factor present in human and bovine milk, and compare the enterocyte assay with the fibroblast assay system used by Klagsbrun (5).

Although the mechanisms by which lactoferrin may stimulate the production of DNA in crypt cells have not been described, a similar protein, transferrin, is known to have a stimulating effect in a variety of cell lines. The two proteins, however, are immunologically distinct. Transferrin is an essential component of highly defined tissue culture media with a requirement of less than 10 μg/ml for most cell lines. Whether this property of transferrin is attributable to the iron or to the apotransferrin protein has not been determined (19). In the cell lines studied thus far, an exclusive receptor is present for either lactoferrin or transferrin (20). Although transferrin and lactoferrin are not interchangeable, we have discovered that lactoferrin has a role parallel to that of transferrin in vitro and in vivo.

We have discovered that lactoferrin both human and animal stimulated thymidine incorporation into DNA by rat or pig crypt enterocytes. Human milk is known to stimulate thymidine uptake in a variety of fibroblast cell lines. The factors responsible for the initiation of mitosis have been identified in part. EGF was the first described and is the best known active factor in human milk. Receptors at the plasma membrane of 3T3 fibroblasts bind EGF (epidermal growth factor) and internalize it for subsequent nuclear binding. This mechanism requires 12 to 14 hours for completion when confluent fibroblast cultures are stimulated (16). In the assay with rat crypt cells, the DNA was harvested after only one hour of incubation. The short incubation may be one reason for the failure of EGF to stimulate enterocytes. The cells in the crypt cell assay may have been conditioned in vivo by EGF before they were harvested for the in vitro bioassay (17).

Klagsbrun and coworkers (18) have identified three factors in human milk which stimulate cell proliferation. The 3T3 cell line responds in vitro to whole human milk and to purified fractions. Klagsbrun's fractions I and II and EGF accounted for 5, 20, and 75%, respectively, of the 3T3 stimulation by human milk. Both larger fractions are broken down to smaller $M_r$ fractions under denaturing conditions. Fraction II is resolved by isoelectric focusing into two fractions with different pI. Based on the reported $M_r$ and PI, none of Klagsbrun's fractions appear to be intact lactoferrin. The cathodic protein in his factor II may be a fragment from intact lactoferrin, but the relative resistance of lactoferrin to proteolysis makes this possibility unlikely. Assays with 3T3 cells confirmed (data not shown) that fractions of human colostrum stimulate thymidine incorporation in this cell line. Human lactoferrin, however, does not promote growth in the 3T3 bioassay which is sensitive to EGF. The absence of sensitivity to lactoferrin in the 3T3 cell line explains why previous investigators have not observed its stimulation of thymidine incorporation in this fibroblast system.

Bovine lactoferrin purified by two different commercial processes is active in the crypt cell bioassay. This is in contract to the lack of stimulatory activity in cow's milk-based infant's formulas. The lactoferrin was from bovine colostrum and bovine mature milk and was acquired from Sigma Chemical Co., St. Louis, Mo.

The biological significance of lactoferrin-induced thymidine incorporation in rat and pig crypt cell DNA has not been elucidated previously. What is clear, however, is that lactoferrin is inactive in 3T3 cell lines which are sensitive to EGF (FIG. 9) and responsive to Klagsbrun's fractions I and II and that EGF is inactive in the crypt cell bioassay sensitive to lactoferrin (FIG. 1).

PRIOR ART STATEMENT

A preliminary search was made of pertinent art in the U.S. Patent Office with the following results:

U.S. Pat. No. 4,216,236 discloses a prepared infant formula from a nutritional point of view.

Archives of Disease in Childhood, 1980, 55, 417–421 discusses lactoferrin in human milk, its role in iron absorption and protection against enteric infection in the newborn infant.

Chemical Abstracts, 95–113091k (1981) reviews factors of milk, including lactoferrin which protect against intestinal infection in the newborn.

Chemical Abstracts, 104–223816n (1986) discusses preparation of fat and protein from banked human milk and its use in feeding very low-birth-weight infants.

The following Chemical Abstracts (CA) citations relate generally to lactoferrin in human milk, properties of transferrin, vitamin D's in cow's milk, infant formulas and breast milk during different stages of lactation, the role of lactoferrin in iron absorption and its relation to nutritional status and antimicrobial factors in whole saliva in infants.

CA 89–144306q (1978); CA 93–42320e (1980); CA 97–180804z (1982); CA 99–155959n (1983); CA 99–171500m (1983); CA 101–190192p (1984); CA 103–70198q (1985); and CA 104–49711n (1986).

None of the foregoing discloses or suggests that milk lactoferrin, human and nonhuman animal, promotes gastrointestinal tract growth in newborn infants which may be given separately as a dietary supplement or incorporated into infant formulas of all types, thus assisting in the management of short gut syndrome, reducing chronic diarrhea, and avoiding, at least to some extent, chronic intractable diarrhea of the infant.

SUMMARY OF THE INVENTION

The present invention is based on the discovery that lactoferrin plays a role similar to that documented in vivo for EGF in the regulation of mucosal growth in the intact animal. This trophic effect on intestinal mucosa is the third nutritional function discovered for this human milk protein. Accordingly, the present invention is directed to providing milk lactoferrin, human and nonhuman animal, to newborn human infants and newborn animals as a dietary ingredient promoting the growth of their gastrointestinal tract immediately on birth. The milk lactoferrin can be included in all infants' formulas and can be given to the infant separately from the formula which stimulates intestinal growth and thus reduces chronic diarrhea and assists in the management of short-gut syndrome and avoid, at least to some extent, chronic intractable diarrhea of the infant.

The amount of lactoferrin given to the infant, either in an infant formula or separately from an infant formula, preferably is comparable to that found in human colostrum, which is up to about 7 grams per liter. The milk lactoferrin may be incorporated into all human infant formulas, such as cow milk based and soy based infant formulas. The Process of obtaining the milk lactoferrin, and the milk from which the lactoferrin is obtained should not be treated, such as by pasturization, which destroys the effectiveness of the milk lactoferrin. The milk lactoferrin need not be absolutely pure, but the purer it is the more active is the milk lactoferrin. Of course, no toxic substances should be present.

The present invention is also directed to a method of treating a human infant for diarrhea by feeding the infant purified milk lactoferrin in a pharmacological amount to stimulate intestinal growth and recovery of the infant, either by incorporating the lactoferrin in an infant formula or by feeding the lactoferrin separately to the newborn infant. Because the biological response to human lactoferrin is assayable in rat and pig crypt enterocytes, it is also reasonable to use this material to stimulate intestinal growth and recovery in often nonruminant mammalian species such as pigs.

It is therefore an object of the present invention to stimulate intestinal growth of human newborn infants by supplementing their diet with a pharmacological amount of lactoferrin effective to stimulate their intestinal growth.

It is a further object of the present invention to stimulate intestinal growth of nonhuman animal newborn infants by supplementing their diet with a pharmacological amount of lactoferrin effective to stimulate their intestinal growth.

It is a further object of the present invention to provide an infant formula containing human or nonhuman animal milk lactoferrin effective for and in an amount sufficient to promote gastrointestinal tract growth in newborn human infants.

It is a further object of the present invention to provide a nonhuman animal infant formula containing human or animal milk lactoferrin effective for and in an amount sufficient to promote gastrointestinal tract growth in nonhuman infants.

It is still a further object of the present invention to provide an infant formula which includes such milk lactoferrin in an amount comparable to that found in human colostrum.

It is a still further object of the present invention to provide an infant formula which includes human milk lactoferrin comparable to from about 0.1 to about 3 grams per liter in human colostrum.

It is a still further object of the present invention to provide human or nonhuman animal milk lactoferrin containing infant formulas of all types, such as cow milk based and soy based, which promotes gastrointestinal tract growth in the newborn infant.

It is still a further object of the present invention to provide a method of treating an infant for diarrhea by supplementing the diet of the infant with human or nonhuman animal milk lactoferrin in amounts comparable to that contained in human colostrum.

It is still a further object of the present invention to provide such a method in which the newborn human infants are supplemented with human or nonhuman animal milk lactoferrin in amounts comparable to 0.1 to 3 grams per liter in human colostrum.

Other and further objects, features, and advantages appear throughout the specification and claims.

DESCRIPTION OF PRESENTLY PREFERRED EMBODIMENTS

Figure 1:
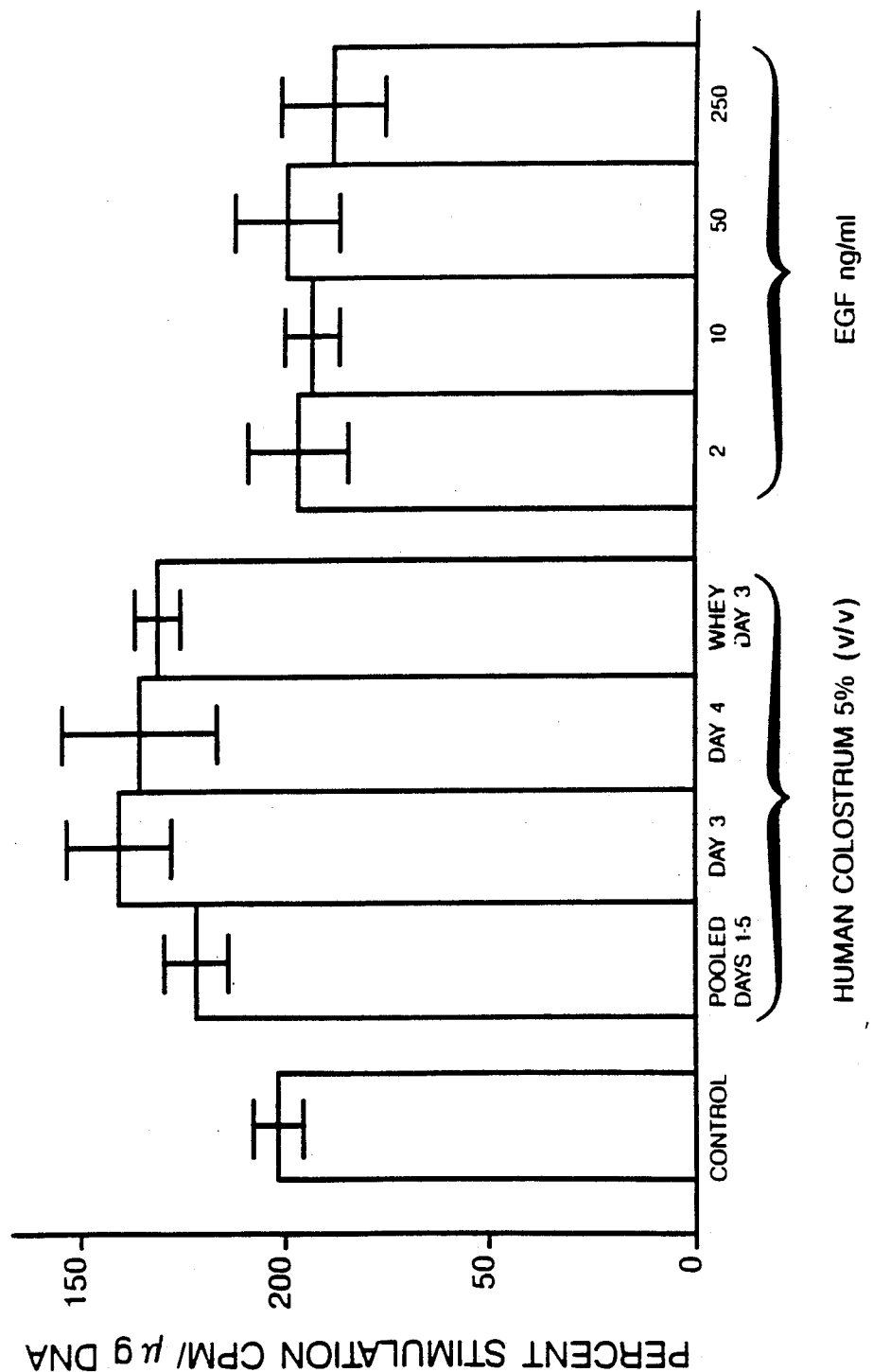
FIG. 1 is a graph illustrating that EGF is inactive in the crypt cell bioassay sensitive to lactoferrin.

As previously mentioned, the present invention is directed to milk lactoferrin as a dietary supplement to promote gastrointestinal tract growth or recovery in human infants and newborn nonhuman animals. The milk lactoferrin may be human or nonhuman animal. The milk containing the lactoferrin cannot be processed, such as by pasturization, or the lactoferrin extracted or purified by a process which destroys the effectiveness of the lactoferrin to promote gastrointestinal tract growth or recovery in infants. The milk lactoferrin may be given to the human infants and newborn animals separately as a supplementary diet or it can be incorporated into infant formulas of all types in which the lactoferrin will go into solution. These include cow milk based and soy based infant formulas.

The lactoferrin should be given in an amount, either separately or in a human infant or newborn animal infant formula, comparable to that found in human colostrum, which in general is about 1 to about 3 grams per liter. The amounts will vary effectively depending upon the purity of the milk lactoferrin, which affects its activity. As previously mentioned, in newborn animals who are nursed by their mother, there is a substantial growth, approximately 8 to 10 inches of the intestines of the infant within the first few days after birth. In a large number of newborn infants, who are not nursed by the mother but are placed on an infant formula, this growth during the first few days may not occur, and the infant may develop chronic intractable diarrhea which must be managed for a period of 3 or more months at considerable expense and discomfort to the infant. By giving the non-nursed young infant or newborn animal milk lactoferrin, either separately or in an infant formula, in amounts comparable to those in colostrum, intestinal growth of the newborn is stimulated which reduces the occurrence of chronic diarrhea, assists in the management of short-gut syndrome, and facilitates recovery, at least to some extent, from chronic intractable diarrhea of the infant.

Another aspect of the present invention is the method of treating a human or nonhuman infants for diarrhea which comprises supplementing the diet of the infant with milk lactoferrin in a pharmacological amount to stimulate intestinal growth and recovery of the infant. Again, good results are obtained by giving an amount of milk lactoferrin to the young infant in amounts comparable to that contained in human colostrum, which is about 1 to about 3 grams per liter in human colostrum. Significantly detectable results, however, have been obtained with as little as 0.1 grams per liter or 0.1% lactoferrin.

Lactoferrin is a glycoprotein of known structure (21, 22) with a $M_r$ of approximately 76,000 and a pI of 8.7 (23). It is present in human milk at a concentration ranging from 1 to 3 g/L (24). Lactoferrin is known to have two functions in the gastrointestinal tract (19). It has an affinity for iron 300 times that of serum transferrin (25). Iron binding occurs on two sites of the molecule and persists after digestion of the fragments to approximately 40,000 $M_r$ (26). The presence of lactoferrin is believed to account for the superior absorption of iron from human milk (27). Lactoferrin also has a bacteriostatic effect on organisms present in the human bowel. The antimicrobial activity is dependent upon the desaturation of iron binding sites (28, 29). Lactoferrin in human milk is less than 5% saturated with iron (24).

The milk lactoferrin can be obtained from any human and nonhuman source in which the lactoferrin is effective to stimulate gastrointestinal growth. The presently preferred sources are human and bovine.

As previously mentioned, the present invention contemplates human infant and newborn animal (nonhuman) formulas of all types in which milk lactoferrin is soluble. The following Table 1 sets forth a representative list of infant formulas available on the market to which the inclusion of milk lactoferrin is advantageous.

If lactoferrin is the mucosal growth factor in maternal fed animals, it should be absent from formulas and its supplementation should increase DNA synthesis to a level observed with mature maternal milk. The commercially available formulas (Table 1) have been tested in the assay system and demonstrate that the addition of lactoferrin at the concentration present in human colostrum increased thymidine incorporation into DNA (Tables 2, 3, and 4).

TABLE 1

Infant Formulas
Prepared Milks and Milk Substitutes Used in Infant Feeding

| | Normal Dilution kcal/oz | Approximate Percentage Composition in Normal Dilution (Gm/per 100 ml) | | | | | Approximate Electrolyte Composition in Normal Dilution (Milliequivalents per Liter) | | | Milligrams per Liter | | |
|---|---|---|---|---|---|---|---|---|---|---|---|---|
| | | Protein | Carbohydrate | Fat | PUFA | Minerals | Na | K | Cl | Ca | P | Fe |
| Enfamil, Mead Johnson | 20 | 1.5 | 6.9 | 3.8 | 1.11 | 0.3 | 9 | 18 | 12.0 | 460 | 320 | 1.0 |
| Similac, Ross | 20 | 1.5 | 7.2 | 3.6 | 1.4 | 0.33 | 10 | 21 | 14 | 510 | 370 | 1.5 |
| SMA, Wyeth | 20 | 1.5 | 7.2 | 3.6 | 0.49 | 0.25 | 6.5 | 14 | 11 | 443 | 330 | 12.7 |
| Isomil (soy), Ross | 20 | 1.8 | 6.8 | 3.7 | 1.4 | — | 13 | 18 | 15 | 700 | 500 | 12 |
| ProSobee (soy), Mead Johnson | 20 | 2.0 | 6.9 | 3.6 | 1.0 | 0.4 | 13 | 20 | 16 | 630 | 500 | 12.7 |
| RCF (soy), Ross | 20 | 2.0 | 0 | 3.6 | 1.4 | 0.38 | 14 | 20 | 17 | 700 | 500 | 1.5 |
| Nutramigen (casein hydrolysate) Mead Johnson | 20 | 2.2 | 8.8 | 2.6 | 0.3 | 0.5 | 14 | 18 | 13 | 630 | 480 | 12.7 |

TABLE 2

Effect of Infant Formula on Crypt Cell Thymidine Uptake

| Formula | Basal (% stimulation) | n | Lactoferrin Supplemented (% stimulation) | n | P* |
|---|---|---|---|---|---|
| Control | 100 ± 11 | 30 | 188 ± 46 | 32 | .001 |
| Human Milk Mature milk (pooled) | 183 ± 14 | 4 | 199 ± 13 | 4 | NS |
| Supplemented Formula (Enfamil premature formula with powdered skim human milk) | 95 ± 16 | 6 | 138 ± 22 | 6 | .001 |
| Cow's Milk-Based | | | | | |
| Enfamil[2] | 79 ± 11 | 10 | 110 ± 13 | 4 | .01 |
| Enfamil (with Iron) | 89 ± 13 | 4 | 145 ± 5 | 4 | .001 |
| Similac 20[3] | 87 ± 13 | 4 | 158 ± 9 | 4 | .001 |
| Similac with Iron 20 | 96 ± 15 | 4 | 151 ± 13 | 4 | .01 |
| SMA 20 (with Iron)[4] | 89 ± 5 | 4 | 165 ± 20 | 4 | .001 |
| Soy-Based | | | | | |
| Isomil 20[3] (with Iron) | 74 ± 4 | 4 | 141 ± 20 | 3 | .01 |
| Prosobee[2] | 65 ± 5 | 10 | 105 ± 11 | 8 | .001 |

TABLE 2-continued
Effect of Infant Formula on Crypt Cell Thymidine Uptake

| Formula | Basal (% stimulation) | n | Lactoferrin Supplemented (% stimulation) | n | P* |
|---|---|---|---|---|---|
| (with Iron) | | | | | |

*Comparison of basal and lactoferrin-supplemented stimulation; student's t-test.
[1]Mean ± SD
[2]Mead Johnson & Company, Evansville, Indiana
[3]Ross Laboratories, Columbus, Ohio
[4]Wyeth Laboratories, Philadelphia, Pennsylvania

TABLE 3
Inhibition of Crypt Cell Thymidine Uptake by Infant Formulas

| Formula | Basal (% stimulation) | n | Lactoferrin Supplemented (% stimulation) | n |
|---|---|---|---|---|
| Control | 100 ± 8* | 17 | 172 ± 18 | 13 |
| Cow's milk | 86 ± 12[1] | 26 | 146 ± 23[1] | 20 |
| Soy-based | 70 ± 10[1,2] | 18 | 123 ± 21[1,2] | 11 |

*Mean ± SD
[1]Significantly different from Control, P less than .01
[2]Significantly different from cow's milk, P less than .01

TABLE 4
Effect of Hydrolyzed Bovine Casein Formulas on Rat Crypt Cell Thymidine Uptake

| Casein Source | Basal (% stimulation) | n | Lactoferrin Supplemented (% stimulation) | n |
|---|---|---|---|---|
| Control | 100 ± 9* | 17 | 172 ± 23 | 17 |
| Nutramigen[1,2] (Old formulation) | 52 ± 8 | 4 | 67 ± 8 | 4 |
| Nutramigen[1,4] (Improved) | 53 ± 3 | 2 | 102 ± 5 | 2 |
| Unhydrolyzed acid[1,3] casein | 98 ± 11 | 4 | 153 ± 10 | 4 |
| Hydrolyzed acid[1,2] casein | 72 ± 8 | 10 | 110 ± 13 | 10 |

*Mean ± SD solutions added t 5% (v/v)
[1]Mead Johnson & Company, Evansville, Indiana
[2]Contains 2.2 g/100 ml hydrolyzed casein
[3]2.2 g/100 ml
[4]1.9 g/100 ml

TABLE 5
Effect of Carbohydrates on Rat Crypt Cell Thymidine Uptake

| | Carbohydrate* | Basal (% stimulation) | n | Lactoferrin Supplemented (% stimulation) | n |
|---|---|---|---|---|---|
| Control | | 100 ± 11.2 | 30 | 188.3 ± 45.9 | 32 |
| RCF | 0 | 78.2 ± 3.2 | 4 | 151.0 ± 15.2 | 4 |
| RCF | Glucose | 79.5 ± 13.6 | 4 | 127.0 ± 17.3 | 4 |
| RCF | Lactose | 107.7 ± 29.3 | 2 | 151.4 ± 4.3 | 2 |
| RCF | Sucrose | 84.3 ± 2.4 | 2 | 127.9 ± 12.6 | 2 |
| RCF | Polycose ® Short | 71.7 ± 6.4 | 2 | 136.4 ± 7.7 | 2 |
| RCF | Polycose ® Long | 79.5 ± 9.3 | 2 | 147.7 ± 18.4 | 2 |

*All carbohydrates were added to RCF at 5.63 gm/100 ml and tested at 5% v/v in the bioassay. Osmolality was adjusted to equal that of RCF + Glucose by adding NaCl or dionized $H_2O$.

TABLE 6

| | PIG - 8 DAYS OLD | |
|---|---|---|
| FRACTION IV C | NORMALIZED (% stimulation) | X ± S.D. |
| | 105.8 | 100 ± 4.5 |
| | 101.4 | |
| | 96.6 | |
| | 96.2 | |

TABLE 6-continued

| | PIG - 8 DAYS OLD | |
|---|---|---|
| FRACTION IV C | NORMALIZED (% stimulation) | X ± S.D. |
| L.F. 100 µg/ml | 116.8 | 118.8 ± 3.8 |
| | 122.6 | |
| | 121.2 | |
| | 114.7 | |

When pooled mature human milk was added to harvested crypt cells and incubated, a significant stimulation of thymidine incorporation into DNA was observed (Table 1). When supplementary lactoferrin was added, there was a modest increase in thymidine incorporation which was not statistically significant. When various cow's milk-based commercially available infant formulas were tested in the crypt cell bioassay, no stimulatory effect was found. The basal thymidine incorporation was equivalent to that observed in control experiments. This was true for a mixture of commercial infant formula with added powdered skim human milk. When supplementary lactoferrin was added to the incubation mixture, significant increase in thymidine incorporation into DNA was observed in each case. This response was independent of the presence of supplementary iron in the formula. The addition of human milk lactoferrin to these infant formulas in a range comparable to that found in human colostrum about 0.2 to 3 grams per liter or from 0.2% to 5% by volume provides good results in promoting the growth of the crypt cells in the rat bioassay described herein. Amounts less than 0.2% or 0.2 grams can be given, for example, detectable stimulation or portions of growth occur as low as 0.1% or 0.1 grams per liter.

Two soy-based commercial infant formulas were tested in the crypt cell assay system. In both cases, the basal stimulation was decreased below that of control experiments. The supplementation of lactoferrin resulted in an increase of thymidine incorporation.

The results from the experiments with cow's milk-based and soy-based formulas are summarized in Table 2. When compared to the control experiments, cow's milk-based formulas demonstrated a significant reduction in basal stimulation. The soy-based formulas demonstrated further reduction in basal stimulation. When supplementary lactoferrin was added, the increased thymidine incorporation demonstrated in the control experiment was observed but there was a quantitative reduction in the percent stimulation in cow's milk formulas and a further reduction in soy-based formulas.

A third category of formulas are those therapeutic formulas designed for use in disoders of digestion and absorption. As an example of this, two hydrolyzed bovine casein formulas were tested in the rat crypt cell bioassay. The first formula revealed a profound depression in basal conditions and a block of response to lactoferrin supplementation on thymidine incorporation into DNA (Table 3). This formula has been modified by replacing the sucrose with small molecular weight starches (corn syrup solids). The depression of basal stimulation was still observed with this new formula; however, lactoferrin supplementation did result in a significant increase in thymidine uptake into crypt cell DNA. Acid casein used as raw material and hydrolyzed acid casein used in both the old and new formulations, were also tested. Basal stimulation was not suppressed by the unhydrolyzed acid casein and response to lactoferrin supplementation was not different from control. The hydrolyzed acid casein depressed the basal stimulation but did not suppress response to lactoferrin supplementation. The response to lactoferrin supplementation, however, was less than that observed with the control experiments.

Figure 10:
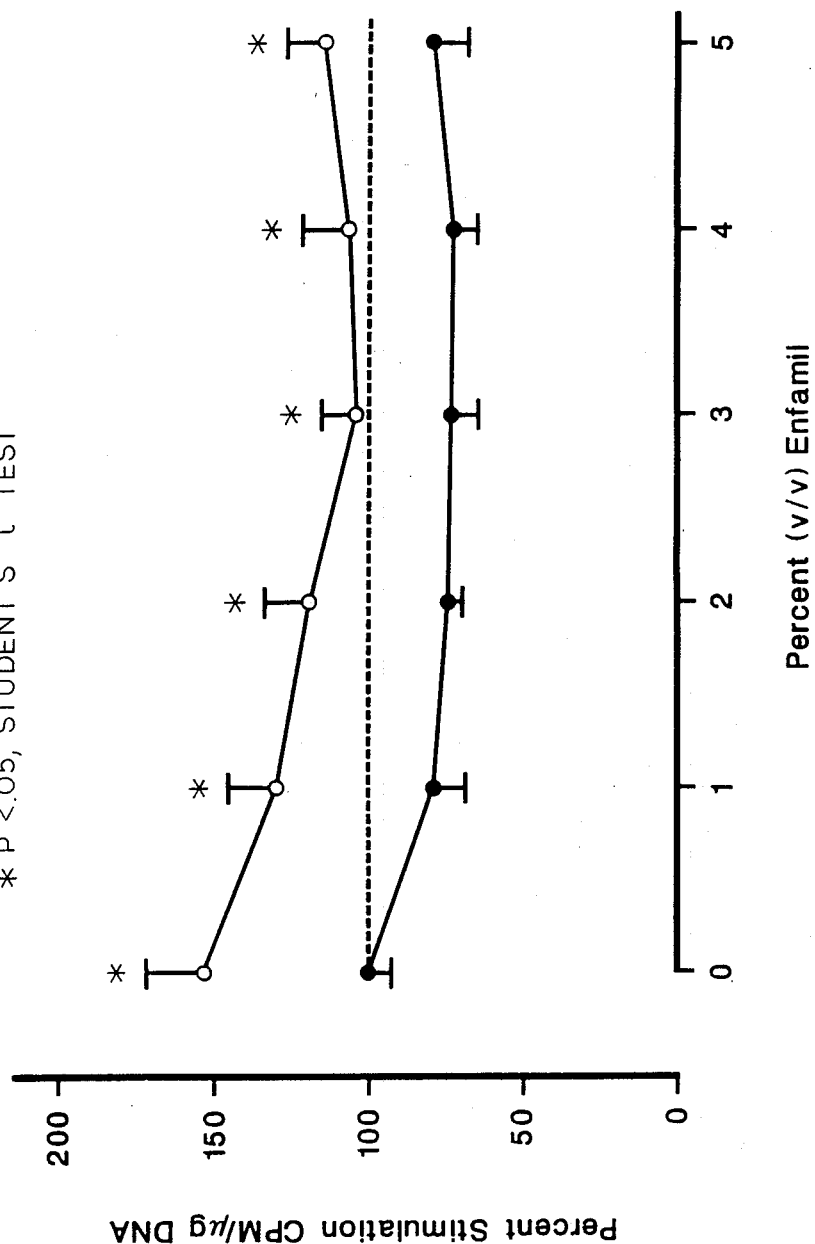
FIG. 10 is a graph demonstrating the suppression of the basal thymidine incorporation into DNA by Enfamil, a cow's milk-based commercial infant formula. There is a significant stimulation of thymidine incorporation in response to 200 or 400 μg of human lactoferrin supplementation to the bioassay.
Figure 11:
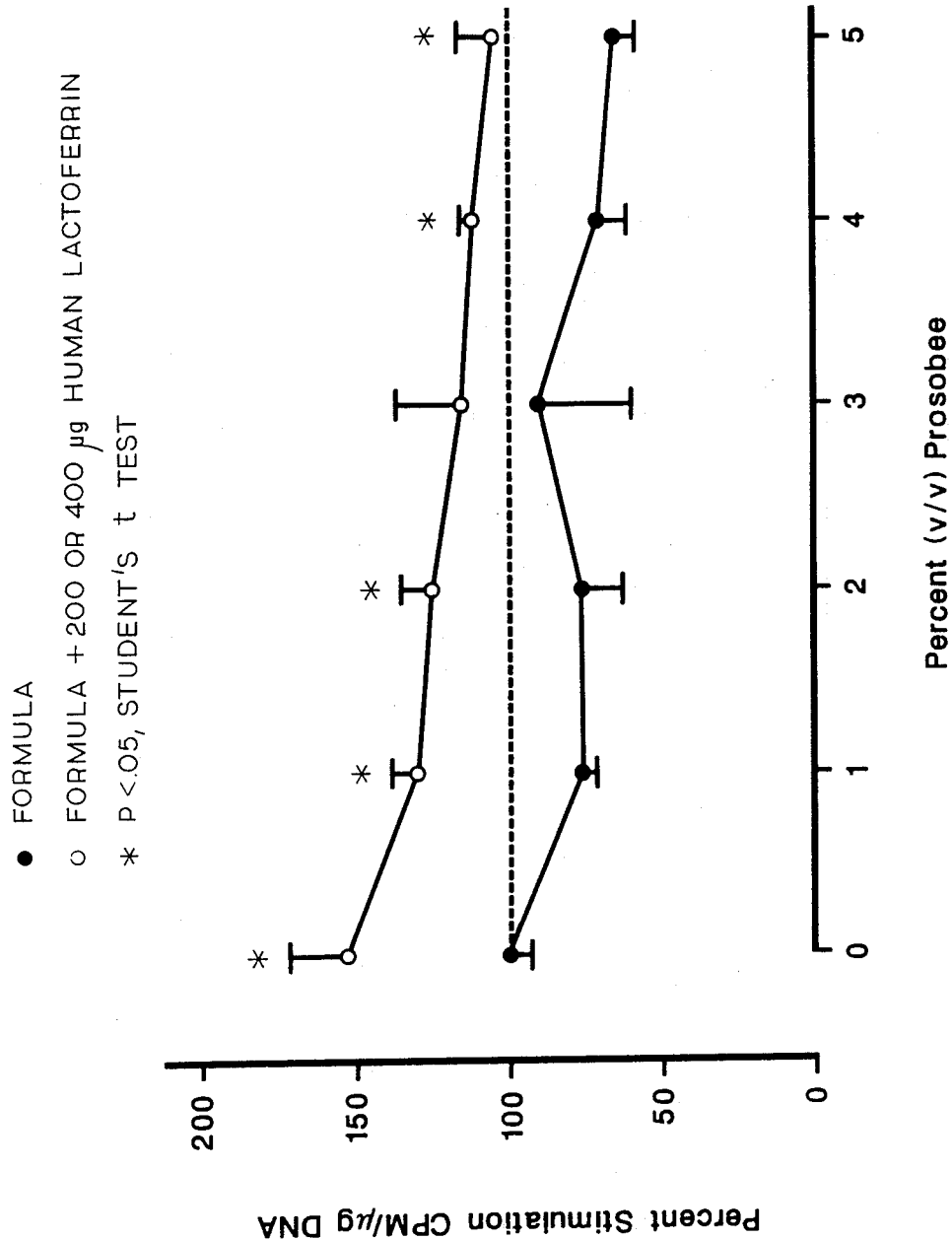
FIG. 11 is a graph, and as in FIG. 10, demonstrates that there is a reduction in the basal thymidine incorporation when Prosobee, a soy-based formula, is added to the bioassay. There is a significant stimulation of thymidine incorporation when supplemental lactoferrin is added. However, this response is not to the degree seen in the control bioassay without added infant formula.

The above results were based on a 5% volume/volume addition of the infant formulas at the stated concentrations in the incubation tubes. These results were further evaluated by testing the infant formulas at lower concentrations. Representative cow's milk and soy-based formulas were tested in concentrations that ranged from 1-5% volume/volume in the bioassay (FIGS. 10 and 11). Compared to control experiments, a consistent reduction in baseline was observed throughout the range of formula concentrations. The response to supplementary lactoferrin was reduced compared to controls but significant when compared to the basal effect of the added formula. The effect of the formula on basal and stimulated thymidine incorporation into DNA was present at one percent concentration. In the experiments with the cow's milk-based formula, one series of bioassay was conducted with 400 $\mu$g of lactoferrin supplementation instead of 200 $\mu$g. Because the results were not different, they were combined.

Figure 12:
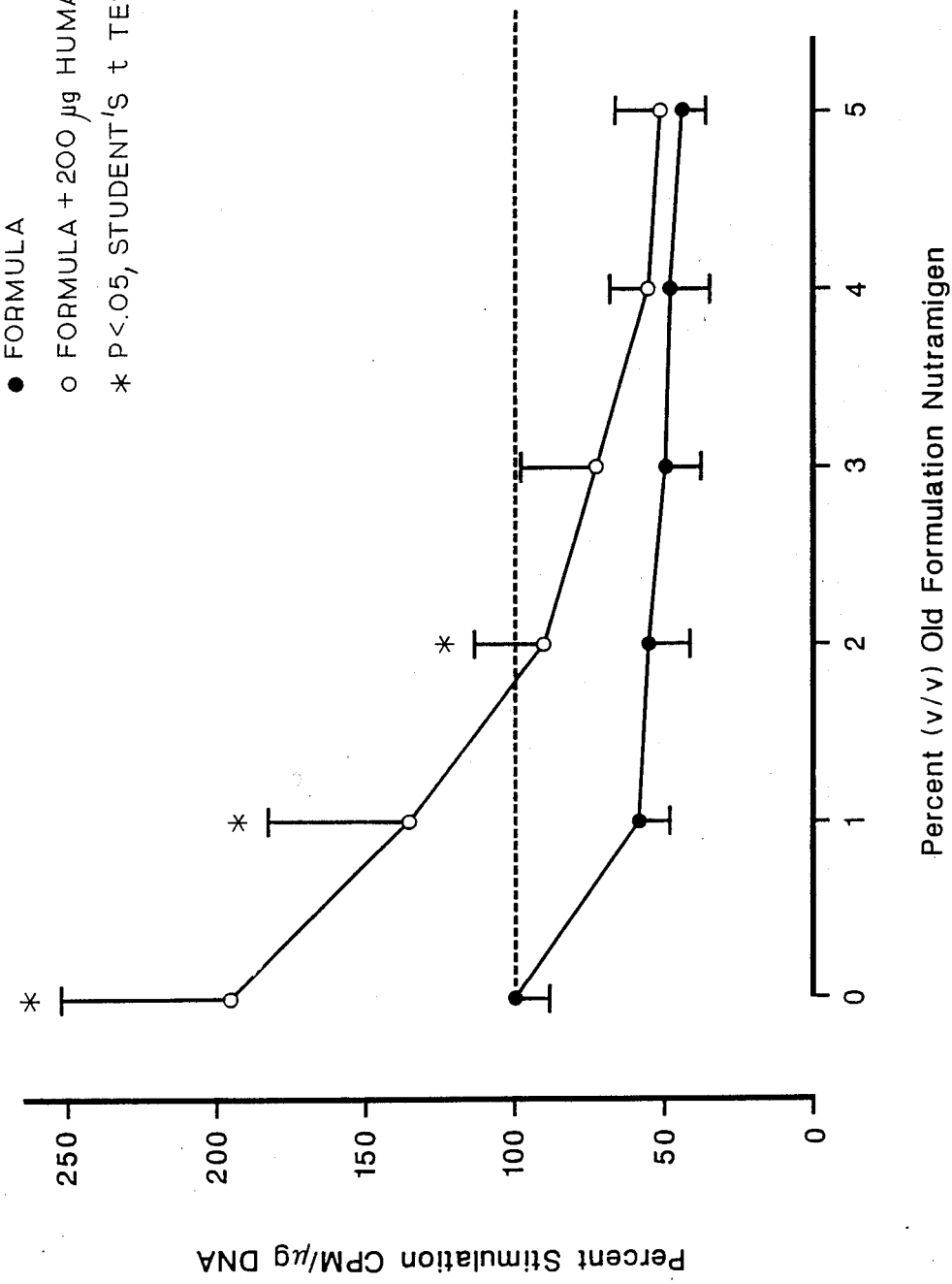
FIG. 12 is a graph of a bioassay of Nutramigen, a hydrolyzed casein formula which contains sucrose. There is a marked suppression of baseline in the presence of Nutramigen and at the higher concentrations, response to lactoferrin supplementation is blocked.
Figure 13:
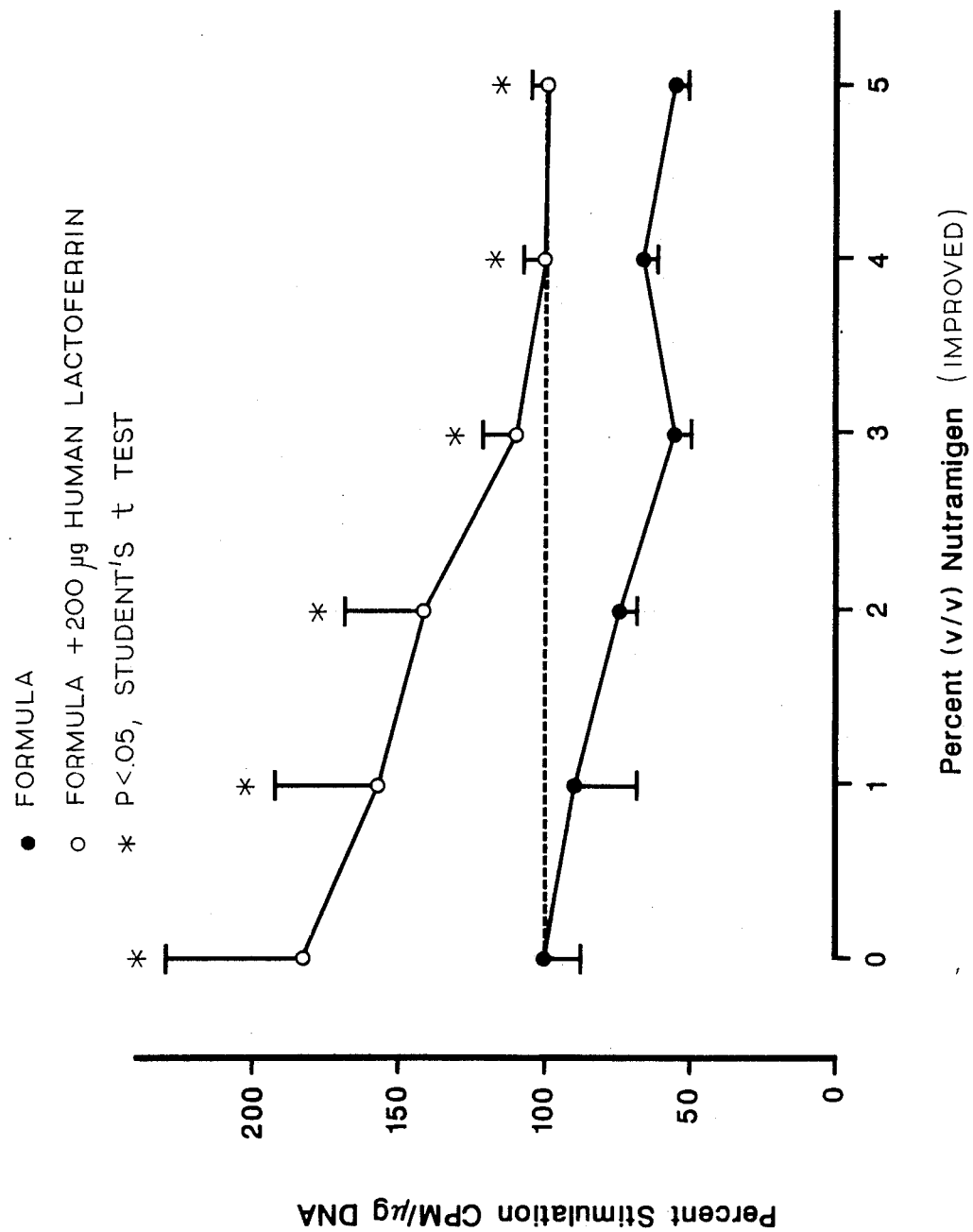
FIG. 13 is a graph illustrating the effects of an improved version of Nutramigen, a hydrolyzed casein formula which has substituted small molecular weight starches for sucrose on the crypt cell bioassay. Note the profound suppression of baseline but the significant response to lactoferrin supplementation even at the higher concentrations of the formula. There is a significant response to the supplementation with human lactoferrin; however, the response is less than that seen in the control experiment without added formula.
Figure 14:
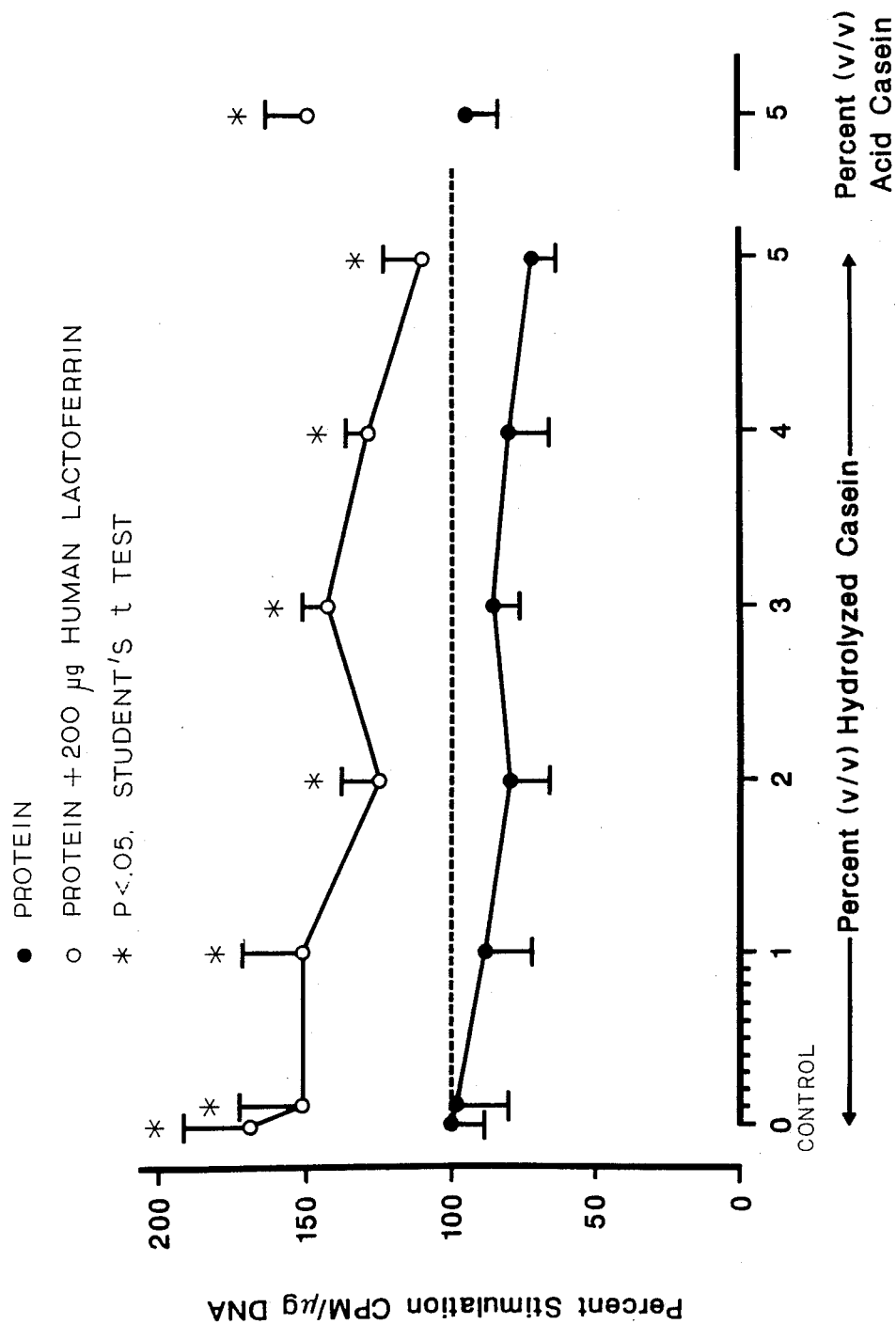
FIG. 14 is a graph of an analysis of the response of the crypt cell bioassay to different concentrations of hydrolyzed casein used in making the formulas described in FIGS. 12 and 13. Note that the acid casein which is used for the production of the hydrolyzed casein does not suppress the baseline and does not suppress the response to lactoferrin supplementation. At concentrations from 1 to 5% the hydrolyzed casein produced from the acid casein suppresses the crypt cell bioassay baseline, but does not suppress the response to the supplemental lactoferrin.

The effect of hydrolyzed casein formulas is indicated in FIGS. 12 and 13. The old formula resulted in a marked suppression of basal and supplemental lactoferrin response at 5% volume/volume concentrations in the bioassay. The basal suppressions persisted at 1 and 2% but the response to supplementary lactoferrin was restored. The response to the new hydrolyzed casein formula was quite different. There was no suppression of the supplementary lactoferrin response at the higher concentrations of formula and there was a loss of the basal suppression at 1% volume/volume in the bioassay. As previously noted, unhydrolyzed acid casein at 5% v/v did not suppress either the basal or supplementary lactoferrin response in the bioassay. To evaluate the possibility that the response to first hydrolyzed formula is due to the hydrolyzed casein, the experiment in FIG. 5 was conducted using the product provided by the formula manufacturer. In concentrations between 1 and 5% the hydrolyzed casein suppressed the basal but did not block the supplementary lactoferrin response. The effect on the basal thymidine incorporation was absent at 0.01% v/v. The bioassay repsonse to the pure hydrolyzed casein is very similar to that observed with the new hydrolyzed casein formula. The possibility that variations in the quality of the carbohydrate present in the formulas might account for these phenomen that was explored (Table 4). In this experiment, a commercially available soy formula manufactured without carbohydrate added was used. As is consistent with the other soy formulas, there was a modest reduction in basal and supplementary lactoferrin stimulation response in the bioasssay. Glucose, lactose, sucrose, and glucose polymers of various average chain length were tested in the bioassay. Glucose and the various starches reduced the baseline modestly but did not block the supplementary lactoferrin stimulation. Lactose appeared to have the least effect on basal and supplementary lactoferrin response in the bioassay.

Figure 15:
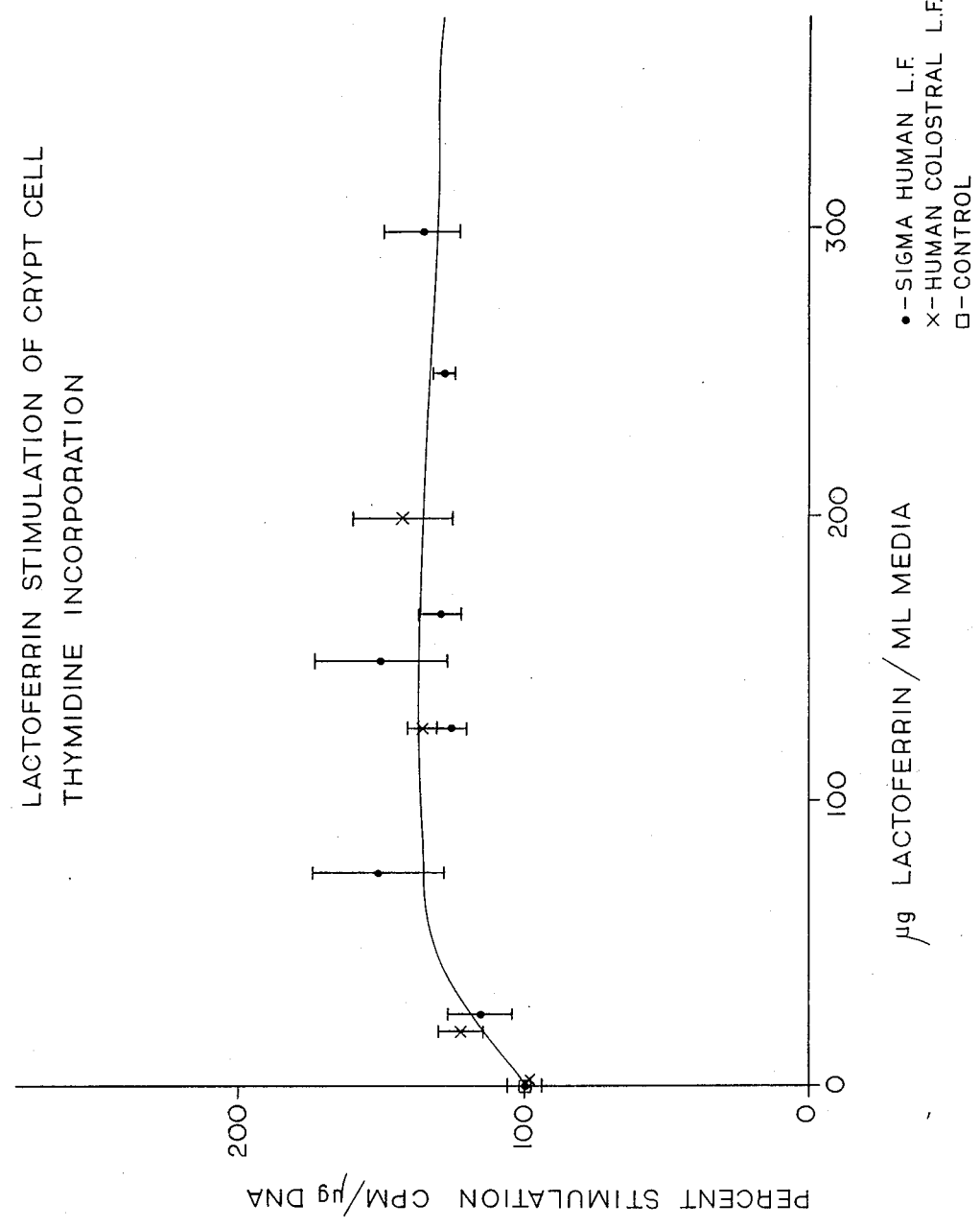
FIG. 15 is a dose response curve of the crypt cell bioassay to two human lactoferrin preparations. The dose in human colostrum is from 100 to 300 μgm/ml. Note that maximal response occurred at 125 μgm/ml and was still detected at 20 μgm/ml.

The dose response of the crypt cell bioassay is shown in FIG. 15. Note that activity was easily detected at concentration of 20 $\mu$g/ml (or 20 mg/L) and that the response peaked at 125 $\mu$g/ml (or 150 $\mu$g/L). The response from 125 to 400 $\mu$g/ml was maximal and had reached a plateau. Two different lactoferrin preparations used in the dose response bioassays are not different.

Figure 16:
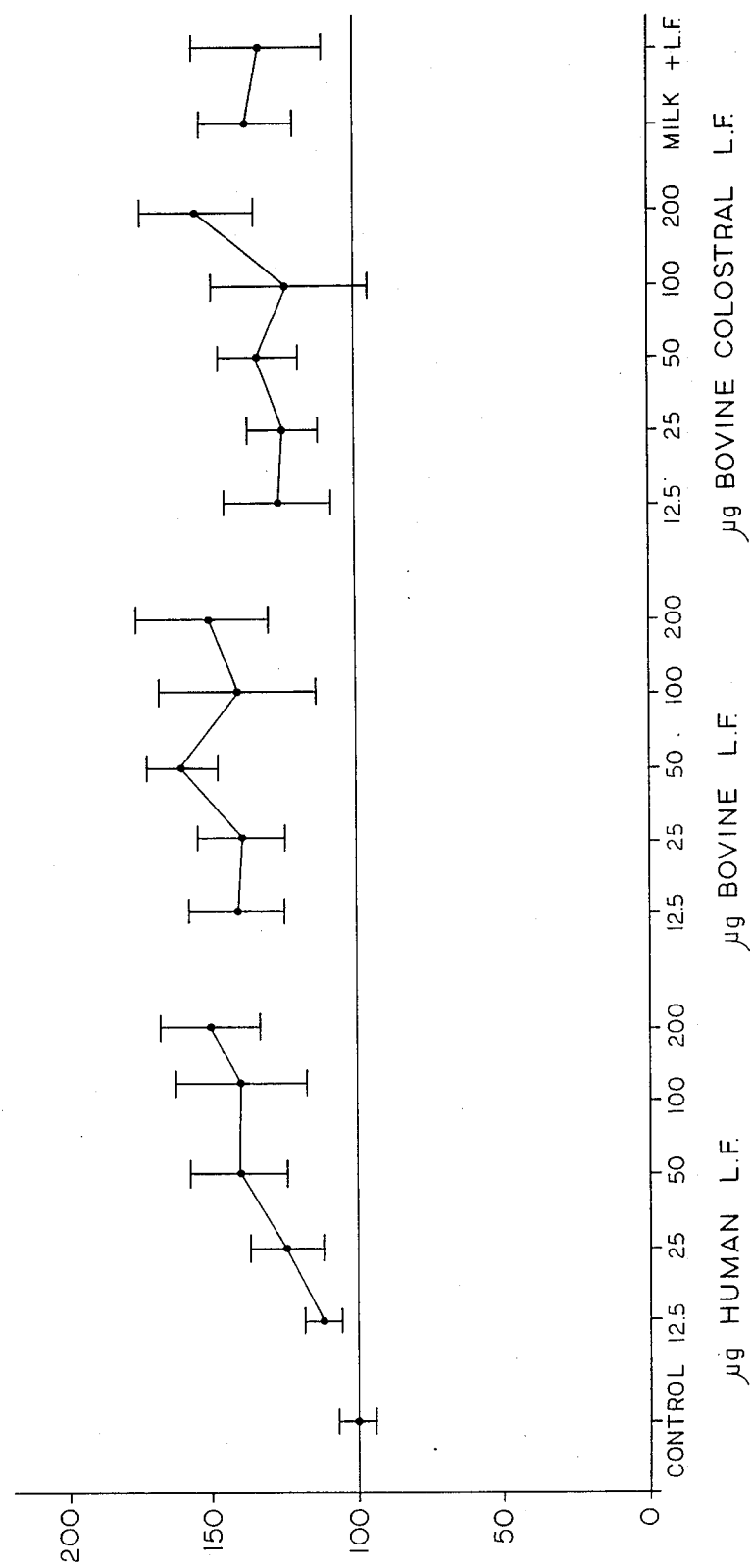
FIG. 16 is a graph illustrating the response of rat enterocytes to human milk lactoferrin and two bovine milk lactoferrin preparations.

The addition of bovine milk lactoferrin to these infant formulas in a range comparable to human milk lactoferrin found in human colostrum also provides good results as shown in FIG. 16. The purity of the human and two bovine milk lactoferrins were not equal; therefore, it is difficult to be confident that there is the same amount of lactoferrin in the human and bovine preparations. It is significant, however, that the bovine lactoferrin is biologically active in vitro.

As previously mentioned, in a search for dietary factors which might stimulate enterocyte proliferation, we developed an assay for thymidine incorporation into deoxyribonucleic acid (DNA) using harvested crypt cells from mature rat small intestine. Human colostrum stimulated a significant increase in thymidine incorporation into rat crypt cell DNA during a 60-minute period of incubation. When the protein with biological activity was purified to a single peak by sequential ion exchange and gel filtration chromatography, it was found to have the characteristics of lactoferrin. The protein was identical to lactoferrin standards by sodium dodecyl sulfate polyacrylamide gel electrophoresis, isoelectric focusing, and double-diffusion immunologic precipitation. All available human lactoferrin stimulated thymidine uptake and all reacted with a lactoferrin polyclonal antibody. Human lactoferrin appears to be a potent activator of thymidine incorporation into DNA in incubated rat crypt cells, a nutritional function not previously reported.

In the description of methods and results, the following abbreviations are used for convenience of disclosure.

Abbreviations $M_r$ molecular weight
EGF epidermal growth factor
PBS phosphate-buffered saline T8 Trowell's T8 medium
EDTA ethylene diamine tetraacetic acid
DNA deoxyribonucleic acid
HPLC high-performance liquid chromatography
SDS PAGE sodium dodecyl sulfate polyacrylamide gel electrophoresis Methods Isolation of crypt cells. Pathogen-free male Sprague Dawley rats (Harlan Industries, Houston, Tex.) were housed under standard conditions for at least two weeks. They were fed rat chow ad libitum. At the time of the study, the rats weighed 375 to 475 g. After the animals were anesthetized with pentobarbitol (50 mg/kg body weight), the jejunum and ileum were removed before the animals were killed. The mucosal cells were sequentially harvested at 37° C. using the method of Harrison and Webster (8) as modified by Bronstein, et. al. (9) in which high frequency vibration at low amplitude is used to shake off mucosal cells. The crypt-cell fraction collected between 12 and 18 minutes of vibration was washed twice in Dulbecco's PBS, suspended in Trowell's T8 medium (Gibco Laboratories, Long Island, N.Y.), and used immediately. An identical method was used to harvest crypt enterocytes for infant pigs.

Differential counts of the harvested cells were made in some experiments using Wright-Giemsa and Papanicolaou stains. Trypan blue exclusion tests also were done on freshly harvested and incubated cells.

Crypt cell bioassay. Isolated crypt cells were used in an assay to measure $^3$H-thymidine incorporation into DNA. T8 medium used for incubation contained 100 U/ml penicillin, 100 $\mu$g/ml streptomycin, 10% fetal bovine serum (Gibco Laboratories, Long Island, N.Y.), and 10 % Ci/ml $^3$H-thymidine. Incubation tubes were placed in a Dubnoff shaking water bath at 37° C. under 95% $CO_2$, and 5% $CO_2$. The tubes contained 0.85 ml medium and 0.05 ml of tested proteins in saline and were preincubated for 1 hour before adding 4 to $5 \times 10^5$ cells in 0.10 ml T8. After incubation for 1 hour, the tubes were placed on ice and 49 ml of PBS #2 (1.0 mM EDTA and 18 mM NaCl) was added. The tubes were centrifuged for 10 minutes at $300 \times g$ and the supernatant decanted. The cells were lysed by adding 0.03 ml 10% (w/v) sodium dodecylsulfate in 0.60 ml buffer (10 mM Tris HCl, 100 mM NaCl, 1.0 mM EDTA, pH 7.4) and the tubes were shaken gently for 15 minutes at room temperature. The samples were deproteinized by adding 0.03 ml of 10 mg/ml crude protease (Sigma Chemical Company, St. Louis, Mo.) and incubated for 30 minutes at 37° C. DNA was determined in deproteinized samples using the method of Labarca and Paigen (10). The buffer used was PBS #2 at pH 7.4 with 2M NaCl and 1.5 g/L EDTA. Calf thymus DNA Type 1 was used as the standard. Hoechst 33258 (Sigma Chemical Company) was used at a concentration of 20 ng/ml. Each acrylic cuvette contained 20 1 of sample or standard and 3.5 ml of buffer with dye. The samples were excited at a wavelength of 354 nm and emission was measured at 450 nm. The assay was linear over the range used.

Radioactivity incorporated into DNA was measured using a modification of the method of Langford and Butel (11). Glass microfiber filter paper strips (2.54 cm $\times$ 20.32 cm) were pretreated with a solution of 1% bovine serum albumin with 0.05M thymidine and 0.5M NaCl and dried 24 hours at 37° C. Each strip was spotted with 300 $\mu$l of deproteinized cell digests and dried overnight at 37° C. The paper strips were agitated using an orbital shaker for 10 minutes in successive washer of cold 10% trichloroacetic acid, 5% trichloroacetic acid, and 95% ethanol. After drying under warm air, the strips were rolled up, put into plastic mini-vials, and covered with 5.25 ml Scintiverse-II (Fisher Scientific, Houston, Texas). Counts per minute (cpm) were determined using a Mark III Scintillation Counter (TM Analytic, Elk Grove Village, Ill.).

Fibroblast bioassay. BALB/c 3T3 mouse embryo cells were grown in Eagle's medium with 10% fetal calf serum, 2 mM glutamine, 4500 mg D-glucose/L, 50 units/ml penicillin, and 50 $\mu$g/ml streptomycin. At passage 86, the cells were treated with trypsin and resuspended at $5 \times 10^4$/ml in medium. Cells (200 $\mu$l) were placed in each well of a 96-well plate (Falcon #3072, Becton Dickinson and Co., Oxnard, Calif.). The cells were incubated at 37° C. in 7% $CO_2$, and were allowed to quiesce. After stimulation with lactoferrin or EGF (25 $\mu$l/well), 25 $\mu$l $^3$H-thymidine at 160 $\mu$Ci was added. Four replicates at each concentration were made. Human AB serum (200 $\mu$g/ml stock) (Gibco, Grand Island, N.Y.) was used as a positive control and 0.9% NaCl as a negative control. All dilutions were made in 0.9% NaCl. After incubation for 48 hours, a Skatron cell harvester (#700 Skatron, Inc., Sterling, Va.) was used to transfer the cells to filter paper. The papers were dried, punched out, and counted in 3 ml Scintiverse II.

Milk collection and processing. Human colostrum was obtained up to five days postpartum. Colostrum and mature milk were collected from individual donors using Egnell breast pumps (Egnell, Inc., Cary, Ill.) and frozen immediately at $-20°$ C. Subsequently, donor samples were thawed, pooled, and refrozen ($-20°$ C. or $-70°$ C.). Colostrum used in the bioassay was thawed and centrifuged at $1000 \times g$ for 10 minutes. The acellular infranatant was added at 5% v/v to the incubation medium.

Isolation from colostrum. The thawed skim colostrum (100 ml) was collected after a 30 minute centrifugation at $10,000 \times g$. Sufficient HCl was added to lower the pH to 4.3. The acidified colostrum was incubated 60 to 90 minutes at 37° C. and was centrifuged at $30,000 \times g$ for 70 minutes at 4° C. The supernatant was collected and dialyzed at 4° C. against 0.5M sodium acetate buffer with 0.2M NaCl (pH 4.2) using tubing with a molecular weight cutoff of 12,000 to 14,000. After dialyzing 5 hours, the sample was transferred to fresh buffer and dialysis was continued overnight. The gel (SP-Sephadex C-50, Pharmacia, Inc.) was equilibrated in the dialysis buffer. Dialyzed colostrum was mixed with an equal volume of gel and allowed to stand for 15 minutes with occasional stirring. Unbound protein was removed by washing, using a buchner funnel and a small volume of buffer. The filtrate was mixed with fresh gel and allowed to bind. Both gels were eluted with the same buffer containing 0.5M NaCl. The eluates were combined and diluted with buffer to 0.2M NaCl, and rechromatographed using fresh gel. The final eluate was placed in dialysis tubing with a molecular weight cutoff of 3,500. Proteins were concentrated by coating the tubing with dry polyethylene glycol 8000. When the sample was 10% of the original volume, 10 ml was applied to a gel filtration column. Separation of proteins was done at 4° C. on a 1.5 cm $\times$ 70 cm column of Sepharose Cl-6B-2000 (Pharmacia, Inc.) using 0.5M sodium acetate buffer with 0.5M NaCl (pH 4.2) as the eluant. The column was calibrated using a mixture of thyroglobulin, gammaglobulin, ovalbumin, myoglobin, and vitamin $B_{12}$ (Gel Filtration Standards, Bio-Rad Laboratories, Richmond, Calif.). Fractions (3.5 ml) were collected every 22 minutes. Fractions containing protein (optical density at 280 nm) were dialyzed against distilled water or 1.0M NaCl and concentrated using Centricon-30 microconcentrators (Amicon Corporation, Danvers, Md.). These fractions were stored frozen at $-20°$ C. Protein concentration was measured using Coomassie blue G-250. Bovine serum albumin was used as a protein standard.

Isolation from mature milk. Mature human milk was pooled, divided into aliquots, and stored at $-20°$ C. Lactoferrin was isolated by the procedure of McKenzie (12). The milk was thawed and centrifuged at 16,000 $\times$ g for 30 minutes at 3° C. The skim was removed and placed into an ice bath. Ammonium sulfate (26.4 g/dl) (Sigma Chemical Company) was added gradually to the skim milk which was stirred mechanically during a 30-minute period. The solution was stirred an additional 90 minutes with the temperature maintained at 0° to 3° C. The precipitate was removed by centrifugation at 14,600 $\times$ g for 35 minutes at 3° C. The supernatant fluid was dialyzed in 0.5M sodium acetate and 0.5M sodium chloride (pH 4.2) at 4° C. The solution was again centrifuged at 14,600 $\times$ g for 35 minutes at 3° C. The supernatant was treated by gel filtration as previously described.

High-performance liquid chromatography. Molecular weight was determined by size exclusion chromatography using a 9.4 $\times$ 250 mm GF-250 column (DuPont Company, Wilmington, Del.) which was equilibrated to 50 mM Tris, 2M NaCl, pH 8.0. The column was calibrated using gel filtration standards (Bio-Rad Laboratories) and was eluted isocratically at a flow rate of 1.0 ml/min using a Hewlett-Packard 1090 A HPLC apparatus with UV detection at 280 nm. All samples were 0.45 micron filtered (Millipore, Bedford, Mass.) before chromatography.

Electrophoresis and immunodiffusion. SDS PAGE was performed using the method of Laemmli (13) on 7.5% total acrylamide gels with 2.67% crosslinker. The electrophoresis was run overnight at room temperature with a constant 40 V. SDS PAGE high molecular weight standards (Bio-Rad Laboratories) were used. The method of Warnick, et. al. (14) was used for isoelectric focusing. The gel had 7.5% total acrylamide and 2.67% crosslinker in 8M urea and was run 15 10° C. Immunologic tests of identity were performed using Ouchterlony's comparative double-diffusion combined system (15). A polyclonal antibody to human lactoferrin (Cooper Biomedical, Inc., Malvern, Pa.) was used. The gels and plates were stained with Coomassie blue.

Lactoferrin and EGF standards. Standard proteins were purchased from the Sigma Chemical Company as freeze-dried preparations. Human lactoferrin was dissolved in 2M NaCl. Aliquots were stored at $-20°$ C. and NaCl was diluted to 0.15M immediately before use. Mouse salivary gland EGF used in the crypt cell assay was dissolved in distilled water, stored frozen, and diluted 1/10 with T8 before use. EGF used in the fibroblast assay was stored frozen in 2M NaCl.

Formula preparation. The infant formulas tested were Enfamil, Enfamil with Iron, Enfamil premature formula (24 calories/fl. oz.), Prosobee and Nutramigen (Mead Johnson & Company, Evansville, Ind.), Similac 20, Similac with Iron 20, Isomil 20 and RCF (Ross Laboratories, Columbus, Ohio), and SMA 20 (Wyeth Laboratories, Philadelphia, Pa.). Two formulations of Nutramigen, a hydrolyzed casein formula, were tested. For the tests of different carbohydrates, a carbohydrate free soya formulation, RCF, was provided by Ross Laboratories. The compositions of these formulas appear in Table 1. Unless otherwise specified, all formulas had 20 calories/fl. oz. and were supplied ready to use. The formulas were centrifuged at 10,000 G, 2° C. for 25 minutes and the skim infranatent was removed and stored frozen ($-20°$ C.) until use.

Protein preparation. Acid casein (Mead Johnson & Company, Evansville, Ind.) was dissolved (2.2 g/100 ml) in phosphate buffer (pH 8.3) and frozen ($-20°$ C.) until use. Casein hydrolysate (Mead Johnson & Company, Evansville, Indiana) was treated in the same manner but water was added to adjust the osmolarity to 0.300. Human lactoferrin (Sigma Chemical Company, St. Louis, Mo.) was dissolved and kept frozen ($-20°$ C.) in 2M NaCl to prevent binding. The lactoferrin was diluted with water immediately before use to make a 4 mg/ml solution in 0.15M NaCl.

Human lactoferrin was isolated from pooled mature milk using a modification of the method described in reference (4). The buffer used was 0.05M TRIS-HCL (pH 8.0) (Sigma Chemical Co., St. Louis, Mo.) with 0.005% sodium azid (Sigma) containing various molarities of NaCl (Sigma). Casein free whey was dialyzed (4° C.) 1/1000 against buffer with no salt then filtered (Whatman) and bound to CM Sepharose Fast Flow (Sigma) equilibrated in the same buffer and packed in a 2.5 cm $\times$ 50 cm Econo-Column (Biorad, Richmond, Calif.). The gel was washed with buffer containing 0.2 NaCl until the absorbance at 280 reached 0, then the lactoferrin was eluted in buffer with 0.7M NaCl. The eluate was dialyzed against 2M NaCl, concentrated and stored frozen ($-20°$ C.) until use.

Purity of the lactoferrin from both sources was monitored by HPLC as in (4).

Human milk preparation. Pooled mature human milk (provided by the Lactation Lab) was thawed and centrifuged at 10,000 g for 15 minutes at 4° C. The skim infranatent was used immediately in the bioassay.

Formula raw materials. The acid casein used as raw materials for the production of hydrolyzed casein and the hydrolyzed casein used in the manufacturer of Nutramigen were provided by Dr. Angel Cordano of Mead Johnson Laboratories. Glucose, lactose and sucrose were obtained from Sigma Chemicals, Inc. Two fractions of Polycose, a partially hydrolyzed corn starch produced by Ross Laboratories were supplied by Dr. Howard Sloan of Columbus, Ohio. The low molecular weight factor had an average glucose equivalence of 7 and the larger molecular weight factor, 70.

Statistical method. Results from the crypt cell bioassay were expressed as cmp/$\mu$g DNA for each incubation tube. At least five controls were run in each assay and the mean of the results was chosen to represent 100% basal stimulation. All values from each experiment were normalized to the mean basal stimulation. Results from the fibroblast bioassay were expressed as cpm/well. Results reported are means $\pm$ standard error (SE).

Results

Crypt cell response to human colostral proteins. Microscopic examination of stained smears from the 12- to 18-minute fraction of the harvested mucosal cells indicated the presence of 0 to 2% lymphocytes. The remaining cells were undifferentiated enterocytes. The cells were 96% viable by Trypan blue exclusion immediately after harvesting and 80% viable after 60 minutes of incubation.

Rat crypt cells incubated with human colostrum had higher rates of $^3$H-thymidine incorporation into DNA than those of controls incubated with 5% (v/v) additional T8 (FIG. 1). Identical results were obtained with a similar fraction of piglet crypt cells. Pooled colostrum, colostrum from individual donors, and casein-free colostral whey were stimulatory. EGF was not stimulatory (FIG. 1).

Figure 3:
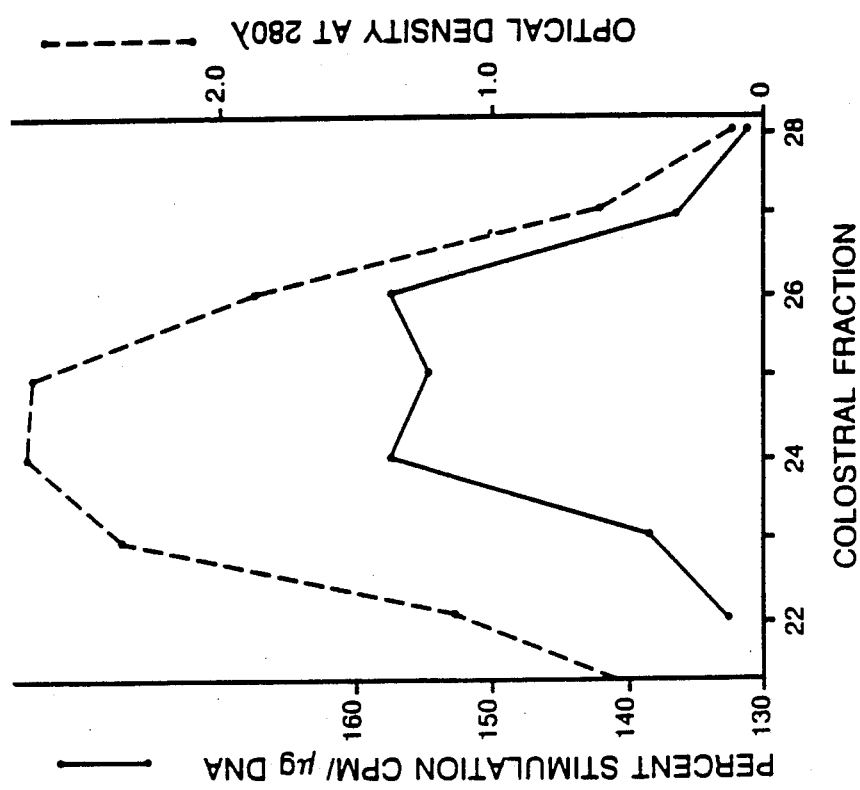
FIG. 3 illustrates crypt cell bioassay: gel filtration fractions tested in duplicate (200 μg/ml). All were more stimulatory than controls (100±7.2).
Figure 2:
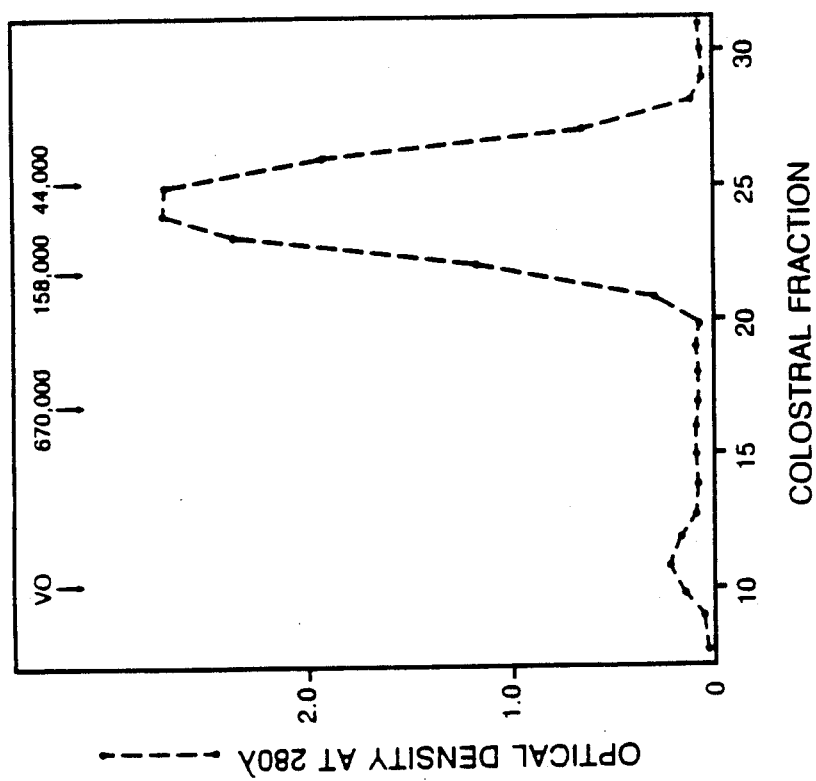
FIG. 2 illustrates gel filtration of colostral protein isolated by ion chromatography: the elution volume and $M_r$ of protein standards are shown at the top of the graph.

Thirty-two fractions were collected from the Sepharose column. Fraction 24 (FIG. 2) contained 13.4 mg of protein and the total protein in fractions 21 to 27 was 51.6 mg. All fractions from the peak stimulated $^3$H-thymidine incorporation (FIG. 3) to levels 30 to 60% higher than controls.

Figure 4:
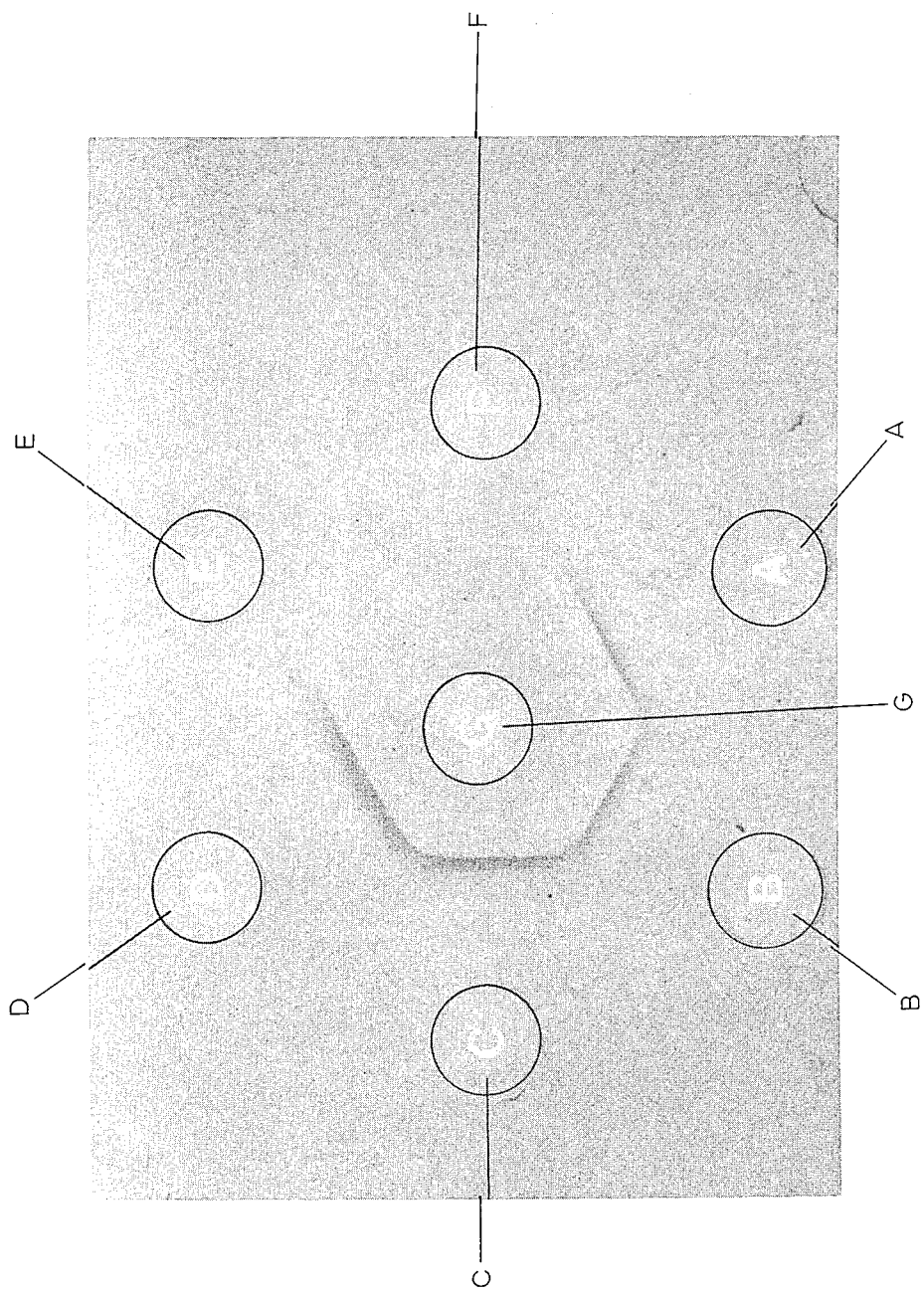
FIG. 4 illustrates ouchterlony plate: two human lactoferrin standards were in wells A and B. Fractions 23 and 24 from gel filtration were in wells C and D. Bovine lactoferrin standards were in wells E and F. Antibody to human lactoferrin was in the center well.
Figure 5:
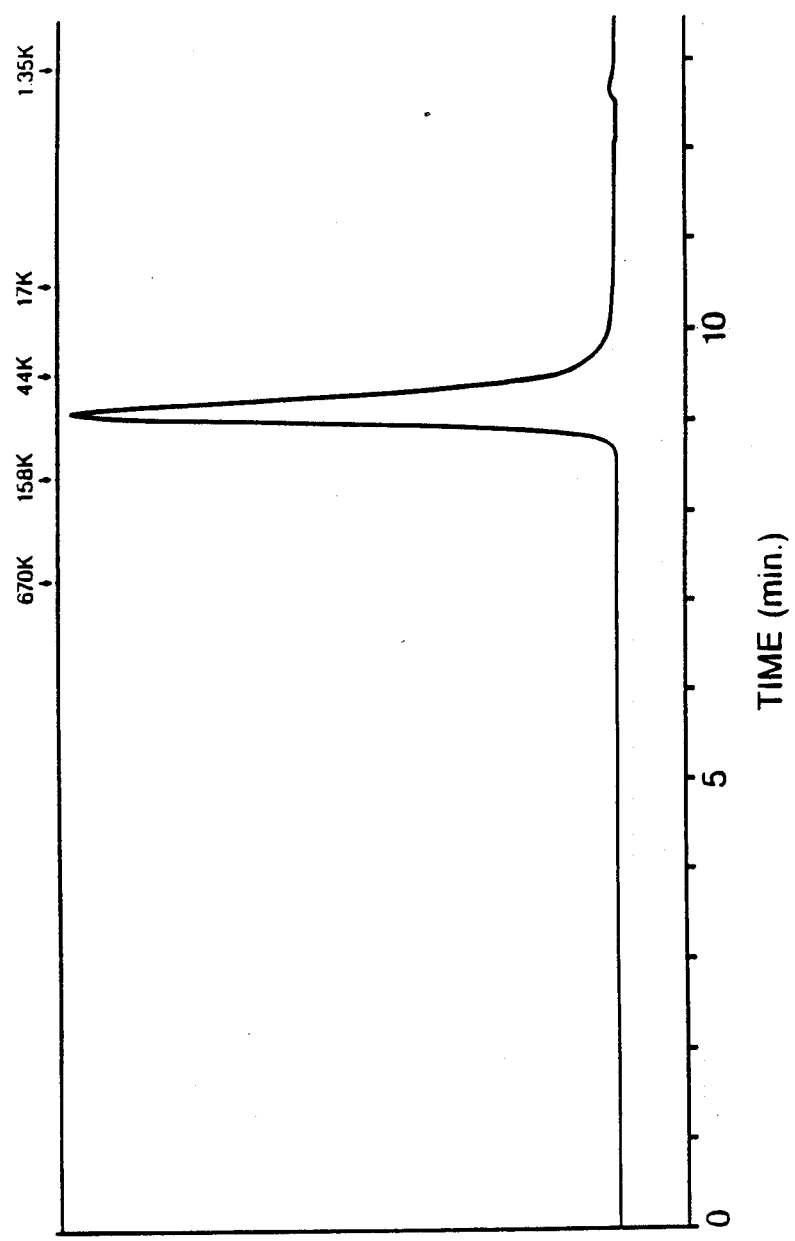
FIG. 5 illustrates HPLC rechromatography of fraction 25 from gel filtration column: the elution time and $M_r$ of calibration protein standards are shown at the bottom and top of the graph.
Figure 6:
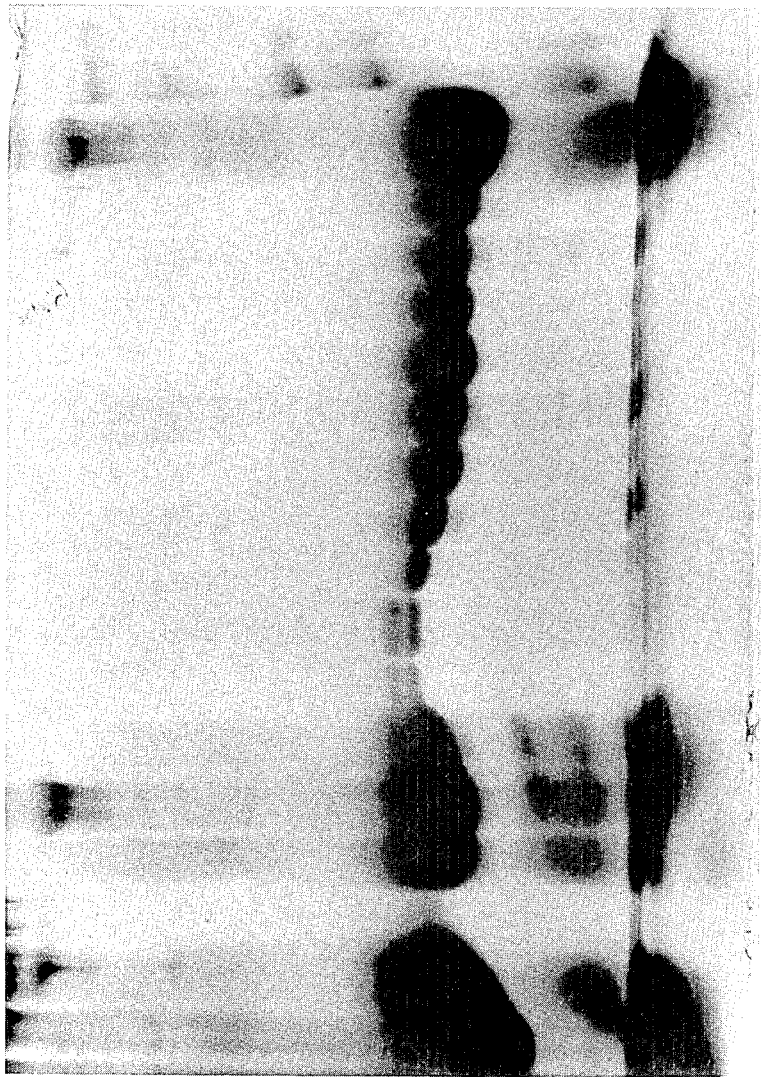
FIG. 6 illustrates SDS PAGE: human colostral proteins. Lane 1 (left), $M_r$ standards; lane 2, skim colostrum; lanes 3 to 10, fractions 21 to 28 from gel filtration of colostral proteins; lanes 11 and 12, human lactoferrin standards.
Figure 7:
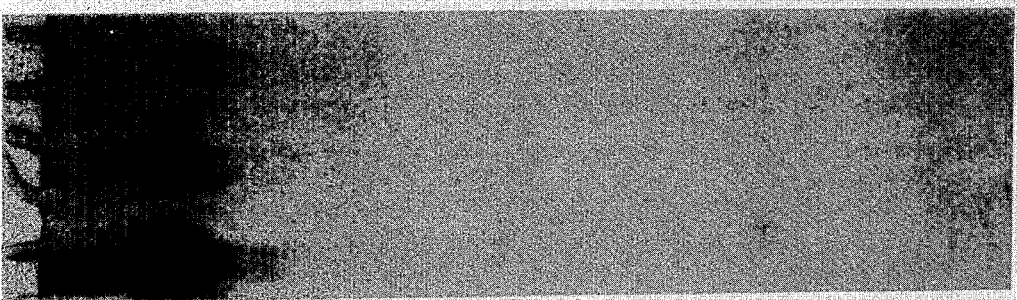
FIG. 7 illustrates isoelectric focusing: human lactoferrin standard in lane 1 and fractions 24 and 25 from human colostrum in lanes 2 and 3.

The color of the concentrated protein fractions from the gel filtration step was light pink. In the immunodiffusion tests using Ouchterlony plates, a line of identity was seen between proteins from the peak and antibodies to human lactoferrin (FIG. 4). Two human lactoferrin standards also formed lines of identity, but bovine lactoferrin standards did not react with the antibody. When tested by HPLC, fraction 25 appeared as a single peak with a molecular weight of approximately 79,000 (FIG. 5). Gel electrophoresis of the fractions and the human lactoferrin standards showed that the major band in all samples migrated at the same rate (FIG. 6). Isoelectric focusing of two peak fractions and the human lactoferrin standard gave similar results (FIG. 7).

Figure 8:
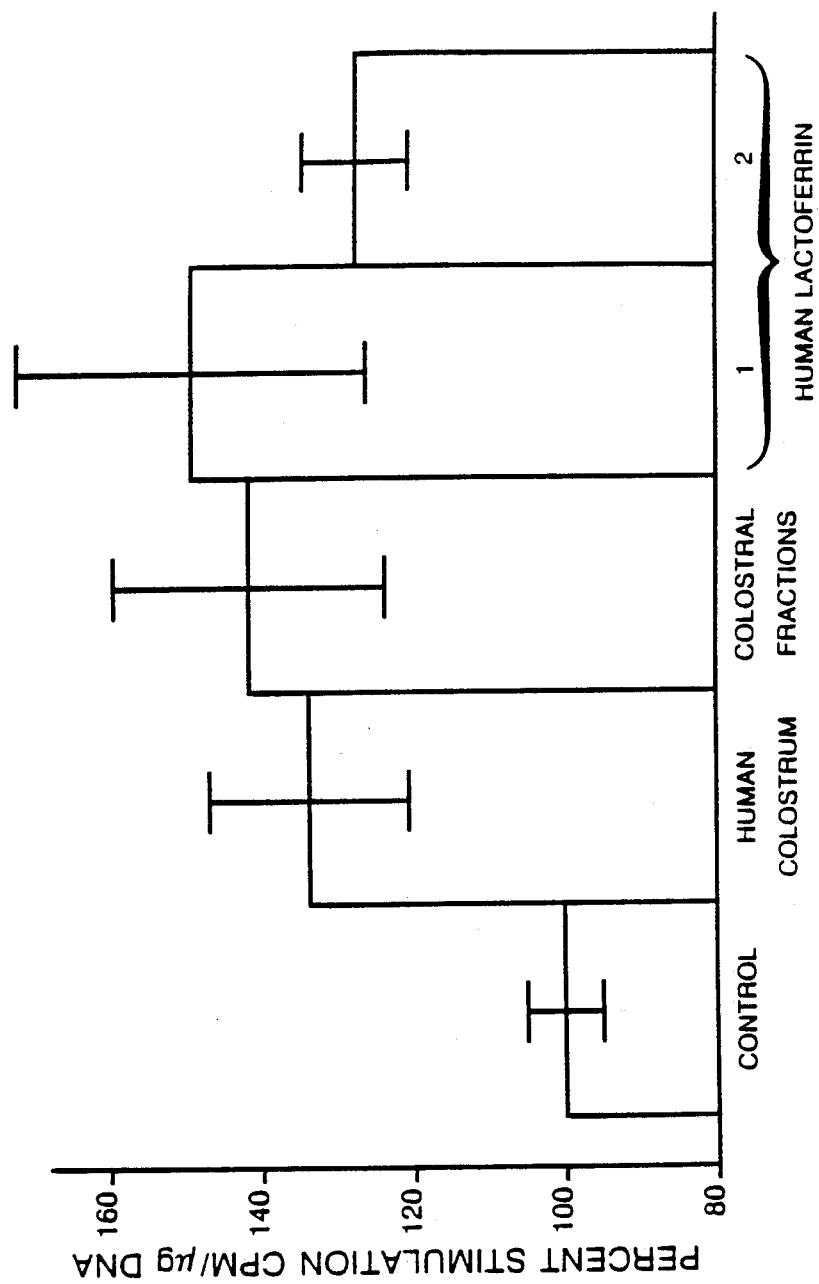
FIG. 8 illustrates rat crypt cell bioassay: human colostrum and two human lactoferrin standards.
Figure 9:
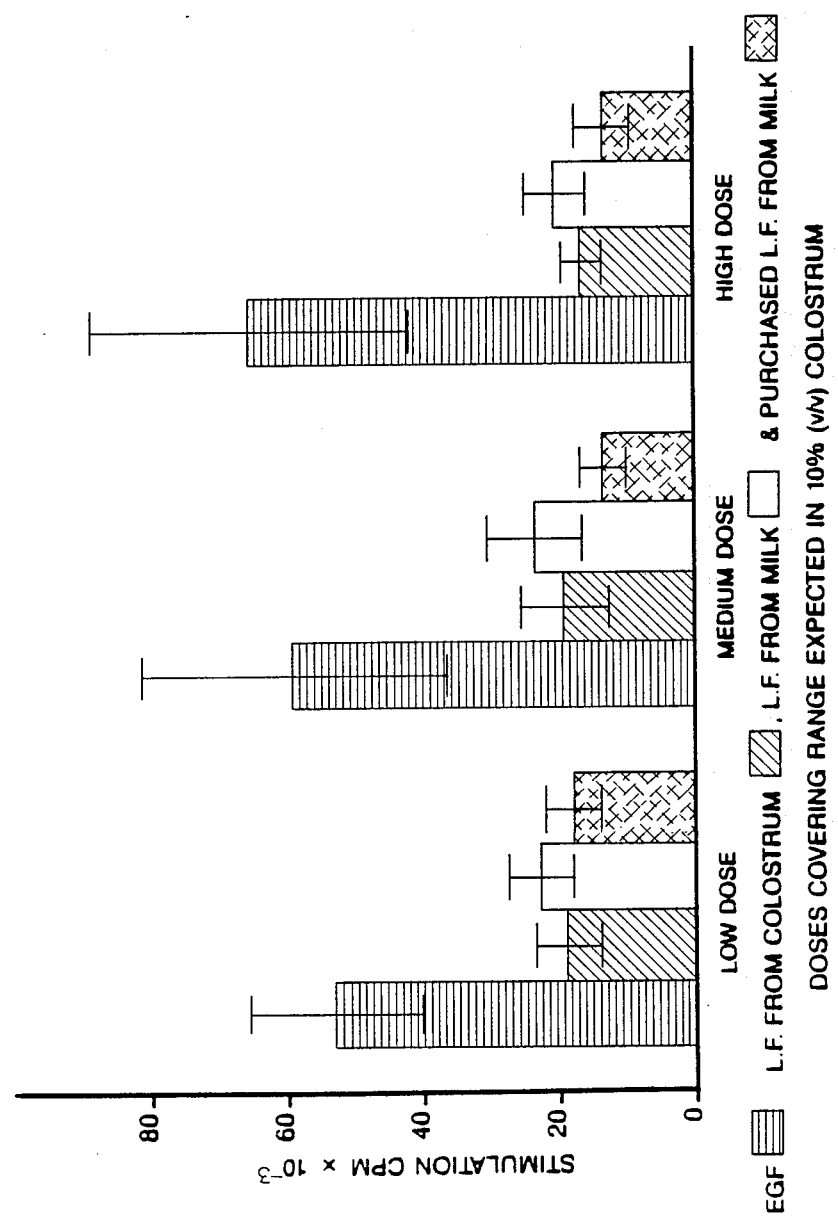
FIG. 9 illustrates fibroblast bioassay: 3T3 cells stimulated with EGF or human lactoferrin in doses covering the range expected in colostrum. Low dose: 1.9 or 3.8 ng/ml EGF, 12.5 or 25 μg/ml lactoferrin; medium dose: 7.5 or 15 ng/ml EGF, 50 or 100 μg/ml lactoferrin; high dose: 30 or 60 ng/ml EGF, 200 or 400 μg/ml lactoferrin.

Crypt-cell and fibroblast response to lactoferrin. Two human lactoferrin standards were tested using the rat crypt-cell assay. Both were stimulatory (FIG. 8) as were skim human colostrum, combined protein fractions 21 to 28 isolated from colostrum, and lactoferrin from mature milk. As shown in FIG. 6, in a similar bioassay using piglet crypt cells the supplementation with 200 µg/ml of human lactoferrin increased DNA incorporation of thymidine from 100±4.5 to 118.8±3.7 percent. In 3T3 cells, although none of the lactoferrin stimulated $^3$H-thymidine uptake over negative control values (20.2±7.8×10$^3$ cpm), EGF at 60 ng/ml resulted in a 75% increase (FIG. 9).

Thymidine incorporation into DNA using harvested crypt cells from mature rat small intestines is an excellent model for the promotion of growth of the gastrointestinal tract of human infants.

The present invention, therefore, is well suited to attain the objects and ends and has the advantages mentioned as well as others inherent therein.

While presently preferred embodiments of the invention have been given for purposes of disclosure, changes and modifications can be made therein which are in the spirit of the invention as covered by the following claims.

What is claimed is:

1. An infant formula containing a pharmacological amount of milk lactoferrin as a sole growth promoter sufficient to promote gastrointestinal tract growth in human infants and infant animals.

2. An infant formula containing a pharmacological amount of milk lactoferrin as a sole growth promoter sufficient to promote gastrointestinal tract growth in infant nonhuman animals.

3. The infant formula of claim 1 where the lactoferrin is bovine lactoferrin.

4. An infant formula containing a pharmacological amount of milk lactoferrin sufficient to promote gastrointestinal tract growth in infant nonhuman animals.

5. The infant formula of claim 4 where the lactoferrin is human milk lactoferrin.

6. The infant formula of claim 4 where the lactoferrin is bovine lactoferrin.

7. An infant formula for promoting gastrointestinal tract growth in infants, including lactoferrin as a sole growth promoter in an amount approximating the lactoferrin content of human colostrum.

8. The infant formula of claim 7 where,
    the amount of lactoferrin ranges from about 0.1 to about 3 grams per liter.

9. The infant formula of claim 1 wherein,
    the infant formula is selected from the group consisting of infant formulas in which milk lactoferrin is soluble.

10. The infant formula of claim 7 wherein,
    the infant formula is selected from the group consisting of infant formulas in which milk lactoferrin is soluble.

11. The infant formula of claim 8 wherein,
    the infant formula is selected from the group consisting of infant formulas in which milk lactoferrin is soluble.

12. A method of stimulating gastrointestinal tract growth in a human infant comprising,
    supplementing the diet of the infant with a pharmacological amount of milk lactoferrin sufficient to stimulate intestinal growth of the infant.

13. The method of claim 12 where the lactoferrin is human milk lactoferrin.

14. The method of claim 12 where the lactoferrin is bovine milk lactoferrin.

15. The method of claim 12 wherein,
    the pharmacological amount of lactoferrin sufficient to stimulate intestinal growth is an amount approximating the amount of the human lactoferrin contained in human colostrum.

16. The method of claim 12 wherein,
    the pharmacological amount of lactoferrin sufficient to stimulate intestinal growth is about 0.2 to about 3 grams per liter.

17. A method of stimulating gastrointestinal tract growth in a infant nonhuman animal comprising,
    supplementing the diet of the animal with a pharmacological amount of milk lactoferrin sufficient to stimulate intestinal growth of the animal.

18. The method of claim 17 where the lactoferrin is bovine milk lactoferrin.

19. A method of stimulating gastrointestinal tract growth in human infant comprising,
    feeding the infant an infant formula containing a pharmacological amount of milk lactoferrin sufficient to promote gastrointestinal tract growth in human infants and infant animals.

20. A method of stimulating gastrointestinal tract growth in a young nonhuman animal comprising,
    feeding the animal an infant formula containing a pharmacological amount of milk lactoferrin sufficient to promote gastrointestinal tract growth in infant nonhuman animals.

21. A method of stimulating gastrointestinal tract growth in a human infant comprising,
   feeding the infant an infant formula for promoting gastrointestinal tract growth in infants, including milk lactoferrin in an amount approximating the lactoferrin content of human colostrum.

22. The method of claim 21 wherein,
   the amount of lactoferrin ranges from about 0.1 to about 3 grams per liter.

23. The method of claim 19 wherein,
   the infant formula is selected from the group consisting of infant formulas in which milk lactoferrin is soluble.

24. The method of claim 21 wherein,
   the infant formula is selected from the group consisting of infant formulas in which milk lactoferrin is soluble.

25. The method of claim 22 wherein,
   the infant formula is selected from the group consisting of infant formulas in which milk lactoferrin is soluble.

26. The infant formula of claim 7 wherein,
   the amount of lactoferrin ranges from about 0.2 to about 3 grams per liter.

27. An infant formula consisting essentially of a pharmacological amount of milk lactoferrin sufficient to promote gastrointestinal tract growth in human infants and infant animals.

* * * * *

REEXAMINATION CERTIFICATE (2325th)

United States Patent [19]

Nichols et al.

[11] B1 4,977,137

[45] Certificate Issued Jun. 28, 1994

[54] LACTOFERRIN AS A DIETARY INGREDIENT PROMOTING THE GROWTH OF THE GASTROINTESTINAL TRACT

[75] Inventors: Buford L. Nichols; Kathryn S. McKee, both of Houston, Tex.

[73] Assignee: Baylor College of Medicine, Houston, Tex.

Reexamination Request:
No. 90/002,908, Dec. 22, 1992

Reexamination Certificate for:
Patent No.: 4,977,137
Issued: Jun. 3, 1987
Appl. No.: 57,562
Filed: Dec. 11, 1990

[51] Int. Cl.$^5$ .................. A61K 37/14; A61K 37/02; A23L 1/305
[52] U.S. Cl. .......................................... 514/6; 514/21; 514/867; 426/74; 426/801

[58] Field of Search ............... 514/6, 21, 867; 426/74, 426/801

[56] References Cited

FOREIGN PATENT DOCUMENTS 2296428 7/1976 France.

OTHER PUBLICATIONS

McMillan et al., Pediatrics, vol. 60 No. 6, 1977 pp.896–900.
Spik et al. Acta Paediatr. Scand. 71:979–985 1982.

*Primary Examiner*—Jacqueline M. Stone

[57] ABSTRACT

Disclosed is milk lactoferrin as a dietary ingredient which promotes growth of the gastrointestinal tract of human infants and newborn nonhuman animals immediately on birth when added to an infant formula or given separately as a dietary supplement thus reducing chronic diarrhea, assisting in the management of short gut syndrome, and avoiding, at least to some extent, chronic intractable diarrhea of the infant.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 4, 7, 12, 17, 19, 20, 21 and 27 are determined to be patentable as amended.

Claims 3, 5, 6, 8-11, 13-16, 18 and 22-26, dependent on an amended claim, are determined to be patentable.

1. An infant formula [containing] *consisting essentially of* a pharmacological amount of *purified* milk lactoferrin as a sole growth promoter sufficient to promote gastrointestinal tract growth in human infants and infant animals, *wherein said lactoferrin and the milk from which it is obtained are not processed.*

2. An infant formula [containing] *consisting essentially of* a pharmacological amount of *purified* milk lactoferrin as a sole growth promoter sufficient to promote gastrointestinal tract growth in infant nonhuman animals, *wherein said lactoferrin and the milk from which it is obtained are not processed.*

4. An infant formula [containing] *consisting essentially of* a pharmacological amount of *purified* milk lactoferrin sufficient to promote gastrointestinal tract growth in infant nonhuman animals, *wherein said lactoferrin and the milk from which it is obtained are not processed.*

7. An infant formula for promoting gastrointestinal tract growth in infants, [including] *consisting essentially of purified milk* lactoferrin as a sole growth promoter in an amount approximating the lactoferrin content of human colostrum, *wherein said lactoferrin and the milk from which it is obtained are not processed.*

12. A method of stimulating gastrointestinal tract growth in a human infant comprising,
  supplementing the diet of the infant with a pharmacological amount of *purified* milk lactoferrin *as a sole growth promoter* sufficient to stimulate intestinal growth of the infant, *wherein said lactoferrin and the milk from which it is obtained are not processed.*

17. A method of stimulating gastrointestinal tract growth in an infant nonhuman animal comprising,
  supplementing the diet of the animal with a pharmacological amount of *purified* milk lactoferrin *as a sole growth promoter* sufficient to stimulate intestinal growth of the animal, *wherein said lactoferrin and the milk from which it is obtained are not processed.*

19. A method of stimulating gastrointestinal tract growth in a human infant comprising,
  feeding the infant an infant formula [containing] *consisting essentially of* a pharmacological amount of *purified* milk lactoferrin sufficient to promote gastrointestinal tract growth in human infants and infant animals, *wherein said lactoferrin and the milk from which it is obtained are not processed.*

20. A method of stimulating gastrointestinal tract growth in a young nonhuman animal comprising,
  feeding the infant an infant formula [containing] *consisting essentially of* a pharmacological amount of *purified* milk lactoferrin sufficient to promote gastrointestinal tract growth in infant nonhuman animals, *wherein said lactoferrin and the milk from which it is obtained are not processed.*

21. A method of stimulating gastrointestinal tract growth in a human infant comprising,
  feeding the infant an infant formula for promoting gastrointestinal tract growth in infants, [including] *consisting essentially of purified* milk lactoferrin in an amount approximating the lactoferrin content of human colostrum, *wherein said lactoferrin and the milk from which it is obtained are not processed.*

27. An infant formula consisting essentially of a pharmacological amount of *purified* milk lactoferrin sufficient to promote gastrointestinal tract growth in human infants and infant animals, *wherein said lactoferrin and the milk from which it is obtained are not processed*

* * * * *